United States Patent [19]
Hock et al.

[11] Patent Number: 5,231,084
[45] Date of Patent: Jul. 27, 1993

[54] COMPOUNDS HAVING A COGNITION ADJUVANT ACTION, AGENTS CONTAINING THEM, AND THE USE THEREOF FOR THE TREATMENT AND PROPHYLAXIS OF COGNITIVE DYSFUNCITONS

[75] Inventors: Franz Hock, Dieburg; Josef Scholtholt, Hanau; Hansjörg Urbach, Kronberg; Rainer Henning, Hattersheim am Main; Ulrich Lerch, Hofheim am Taunus; Wolf-Ulrich Nickel, Bad Soden am Taunus; Wolfgang Rüger, Kelkheim, all of Fed. Rep. of Germany

[73] Assignee: Hoechst Aktiengelsellschaft, Frankfurt am Main, Fed. Rep. of Germany

[21] Appl. No.: 711,719

[22] Filed: Jun. 7, 1991

Related U.S. Application Data

[60] Division of Ser. No. 362,288, Jun. 6, 1989, abandoned, which is a continuation of Ser. No. 226,521, Aug. 1, 1988, abandoned, which is a continuation of Ser. No. 29,905, Mar. 25, 1987, abandoned.

[30] Foreign Application Priority Data

Mar. 27, 1986 [DE] Fed. Rep. of Germany ....... 3610391

[51] Int. Cl.$^5$ .......................... A61K 37/02; C07K 5/06
[52] U.S. Cl. ......................... 514/19; 514/81; 514/91
[58] Field of Search ................... 514/19, 81, 91

[56] References Cited

U.S. PATENT DOCUMENTS

| 4,129,571 | 12/1978 | Ondetti et al. | 260/326.2 |
|---|---|---|---|
| 4,344,949 | 8/1982 | Hoefle et al. | 424/258 |
| 4,350,704 | 9/1982 | Hoefle et al. | 424/274 |
| 4,374,829 | 2/1983 | Harris et al. | 424/177 |
| 4,374,847 | 2/1983 | Gruenfeld | 424/274 |
| 4,374,847 | 2/1983 | Gruenfeld | 514/415 |
| 4,454,292 | 6/1984 | Kim et al. | 548/491 |
| 4,470,972 | 9/1984 | Gold et al. | 424/177 |
| 4,508,729 | 4/1985 | Vincent et al. | 514/419 |
| 4,525,301 | 6/1985 | Henning et al. | 548/411 |
| 4,558,064 | 12/1985 | Teetz et al. | 514/409 |
| 4,558,065 | 12/1985 | Urbach et al. | 514/412 |
| 4,562,202 | 12/1985 | Urbach et al. | 514/423 |
| 4,587,258 | 5/1986 | Gold et al. | 514/412 |
| 4,591,598 | 5/1986 | Urbach et al. | 514/412 |
| 4,614,805 | 9/1986 | Urbach et al. | 548/427 |
| 4,620,012 | 10/1986 | Henning et al. | 548/411 |
| 4,624,962 | 11/1986 | Henning et al. | 548/452 |
| 4,659,838 | 4/1987 | Lerch | 548/452 |
| 4,668,796 | 5/1987 | Geiger et al. | 548/452 |
| 4,668,797 | 5/1987 | Urbach et al. | 548/452 |
| 4,684,662 | 8/1987 | Henning et al. | 548/452 |
| 4,691,022 | 9/1987 | Henning et al. | 548/408 |
| 4,714,708 | 12/1987 | Urbach et al. | 514/412 |
| 4,727,160 | 2/1988 | Teetz et al. | 548/452 |
| 4,808,573 | 2/1989 | Gold et al. | 514/19 |
| 4,818,749 | 4/1989 | Gold et al. | 514/19 |
| 4,822,894 | 4/1989 | Geiger et al. | 548/252 |
| 4,831,157 | 5/1989 | Gold et al. | 548/452 |
| 4,849,524 | 7/1989 | Henning et al. | 548/411 |
| 4,868,307 | 9/1989 | Barton et al. | 546/256 |
| 4,886,827 | 12/1989 | Urbach et al. | 371/37.5 |
| 4,931,460 | 6/1990 | Sudilovsky et al. | 514/19 |
| 5,015,633 | 5/1991 | Sudilovsky | 514/19 |

FOREIGN PATENT DOCUMENTS

81/75949 1/1981 Australia .
(List continued on next page.)

OTHER PUBLICATIONS

U. Schindler et al., Nootropic Drugs: Animal Models for Studying Effects on Cognition, Drug Development Research 4:567–576 (1984).

(List continued on next page.)

Primary Examiner—Lester L. Lee
Attorney, Agent, or Firm—Finnegan, Henderson, Farabow, Garrett & Dunner

[57] ABSTRACT

The invention relates to new comoounds having a cognition adjuvant action, to the use of ACE inhibitors as medicaments having a cognition adjuvant action, to agents containing them, and to the use thereof for the treatment and prophylaxis of cognitive dysfunctions.

2 Claims, No Drawings

FOREIGN PATENT DOCUMENTS

| | | |
|---|---|---|
| 81/77022 | 11/1981 | Australia . |
| 1187087 | 5/1985 | Canada . |
| 1193607 | 9/1985 | Canada . |
| 1197252 | 11/1985 | Canada . |
| 1206478 | 6/1986 | Canada . |
| 0012401 | 6/1980 | European Pat. Off. . |
| 0012845 | 7/1980 | European Pat. Off. . |
| 0018549 | 11/1980 | European Pat. Off. . |
| 0037231A2 | 10/1981 | European Pat. Off. . |
| 0048159 | 3/1982 | European Pat. Off. . |
| 0050800 | 5/1982 | European Pat. Off. . |
| 0050850A1 | 5/1982 | European Pat. Off. . |
| 0051301 | 5/1982 | European Pat. Off. . |
| 0052991 | 6/1982 | European Pat. Off. . |
| 0046953 | 10/1982 | European Pat. Off. . |
| 0065301 | 11/1982 | European Pat. Off. . |
| 0079022 | 5/1983 | European Pat. Off. . |
| 0079521 | 5/1983 | European Pat. Off. . |
| 0079522 | 5/1983 | European Pat. Off. . |
| 0080822 | 6/1983 | European Pat. Off. . |
| 0084164 | 7/1983 | European Pat. Off. . |
| 0090362 | 10/1983 | European Pat. Off. . |
| 0049658 | 4/1984 | European Pat. Off. . |
| 0115091 | 8/1984 | European Pat. Off. . |
| 0196841 | 10/1986 | European Pat. Off. . |
| 0243645 | 11/1987 | European Pat. Off. . |
| 3322530 | 1/1985 | Fed. Rep. of Germany . |
| 813034 | 4/1981 | Finland . |
| 812859 | 3/1982 | Finland . |
| 813283 | 4/1982 | Finland . |
| 813422 | 5/1982 | Finland . |
| 2491469 | 4/1982 | France . |
| 64085 | 4/1981 | Israel . |
| 57-77672 | 5/1982 | Japan . |
| 57-112359 | 7/1982 | Japan . |
| 57-91974 | 8/1982 | Japan . |
| 198702 | 8/1985 | New Zealand . |
| 198535 | 9/1989 | New Zealand . |
| 81/5988 | 8/1981 | South Africa . |
| 83/2229 | 12/1983 | South Africa . |
| 87/2230 | 3/1987 | South Africa . |
| 2086390 | 5/1982 | United Kingdom . |
| 2095682 | 10/1982 | United Kingdom . |

OTHER PUBLICATIONS

R. T. Bartus, et al. Logical Principles for the Development of Animal Models of Age-Related Memory Impairments, Assessment in Geriafric Psychopharmacology, published by Mark Pauley Associates, Inc. 88 Main Street, New Cannan, Connecticut, USA, Dec. 1983, pp. 263–299.

G. Pepeu, The Relationship Between the Behavioral Effects of Cognition-Enhancing Drug and Brain Acetylcholine, Pharmacopsychiat, 22, 116–119, (1989).

Brunner et al., J. Cardiovasc Pharmacol. vol. 7 (Suppl. 1), pp. 2–11 (1985).

Leonard et al., J. Am. Chem. Soc., 77, 439 (1955).

Leonard et al., J. Am. Chem. Soc., 78, 3457 (1956).

Leonard et al., J. Am. Chem. Soc., 78, 3463 (1956).

Leonard et al., J. Am. Chem. Soc., 81, 5627 (1959).

Koelsch et al., J. Org. Chem., 26, 1104 (1961).

Griot et al., Helv. Chim. Acta, 42, 121 (1959).

Bonnett et al., J. Chem. Soc., 2087 (1959).

Battersby et al., J. Chem. Soc., 4333 (1958).

Rosenblatt et al., The Chemistry Of Functional Groups. Supplement F: The Chemistry of Amino, Nitroso and Nitro Compounds And Their Derivatives. Part II, S. Patai, ed., Wiley & Sons: New York 1982, pp. 1100–1104.

L. W. Haynes, Enamines, A. G. Cook, ed., Marcel Decker, Inc.: 1969, pp. 68–79, 261–269, 413.

Fieser & Fieser, Reagents For Organic Synthesis, vol. 1, pp. 644–651 (1967).

Boehme et al., Iminium Salts in Organic Chemistry, Part I (E. C. Taylor, ed.), Wiley & Sons: New York, 1976, p. 143.

S. Dayagi et al., The Chemistry of Functional Groups. The Chemistry Of The Carbon-Nitrogen Double Bond, S. Patai, ed., Wiley & Sons: New York, 1970, p. 119.

W. Greenlee et al., J. Med. Chem., 28, 434–442 (1985).

K. Ogawa et al., J. Chem. Soc., Perkin Trans. I, 3031–3035 (1982).

R. Bacon and D. Stewart, J. Chem. Soc. (C), 1384–1387 (1966).

R. Bacon et al., J. Chem. Soc. (C), 1388–1389 (1966).

Patchett et al., Nature, 288, 280–283 (1980).

Booth et al., Chemistry and Industry, 466–467 (1956).

Booth et al., J. Chem. Soc., Part I, 1050–1054 (1959).

Murakoshi et al., Chemical Abstracts, 61, 9465(e) (1964).

Cushman et al., Fed. Proc., 38 (13), 2778–2782 (1979).

Houben-Weyl, Methoden der Organischen Chemie, 7(2b), 1403–1404 (1976).

FOREIGN PATENT DOCUMENTS

Katritskaya, Dzh. Lagorskaya Khimia Geterosikl. Soedin., Moskow 1963, pp. 155–158.

Anderson, Jr. et al., J. Org. Chem., 43(1), 54–57 (1978).

Bertho et al., Synthesen In Der 2-Azabicyclo[0.3.3]-octan-Reihe, Chemische Berichte, 92(7), 2218–2235 (1959).

Farkas et al., J. Org. Chem., 22, 1261–1263 (1957).

Taylor et al., J. Org. Chem., 38(16), 2817–2821 (1973).

Taylor et al., Heterocycles, 25, 343–345 (1987).

English language translation of Mitzlaff et al., Liebig's Ann. Chem., 1713–1733 (1978).

Chem. Berichte 86: 1524–1528 (1953).

Quarterly Reviews 25: 323–341 (1971).

Chem. Abst. 49/1955/3009c.

Bolis, "Renin Inhibitors" J. Med. Chem. 30, 1729–1737 (1987).

Haber, "Renin Inhibitors", J. Cardiovascular Pharm. S54–S58 (1987).

Plattner, "Renin Inhibitors", 2277–288 (1988) 31.

Denkervalte, Progress in Drug Research, vol. 10 pp. 510–512.

Burger, "Medicinal Chemistry" 2nd edition, 1960 Interscience Publishers pp. 565–601.

COMPOUNDS HAVING A COGNITION ADJUVANT ACTION, AGENTS CONTAINING THEM, AND THE USE THEREOF FOR THE TREATMENT AND PROPHYLAXIS OF COGNITIVE DYSFUNCITONS

This application is a division of application Ser. No. 07/362,288 filed Jun. 6, 1989, which is a continuation of application Ser. No. 07/226,521 filed Aug. 1, 1989, which is a continuation of application Ser. No. 07/029,905 filed Mar. 25, 1987, all now abandoned.

The invention relates to the use of angiotensin converting enzyme inhibitors (ACE inhibitors) or their physiologically tolerated salts as medicaments having a cognition adjuvant action (improving cognitive function) and to the use thereof in the preparation of corresponding pharmaceutical formulations.

Examples of suitable compounds for this novel use are those of the formula I $$X^1-X^2 \qquad (I)$$

in which $X^1$ denotes $$R^3OOC-\overset{*}{C}H-N-\overset{*}{C}-(CHR^1)_m-,$$
$$\quad\;\; | \quad\; | \;\; ||$$
$$\quad\;\; R^4 \;\; R^5 \;\; O$$

or $X^2$ denotes —CH$_2$SH, $$-CH_2-S-\overset{O}{\overset{||}{C}}-R^6, \; -CH_2-\overset{O}{\overset{||}{\underset{|}{P}}}-R^7 \text{ or}$$
$$\qquad\qquad\qquad\qquad\quad OR^8$$

$$-Y^2-(CH_2)_p-\overset{*}{C}H-(CH_2)_n-R$$
$$\qquad\qquad\;\; |$$
$$\qquad\qquad\;\; COOR^2$$

$Y^1$ represents —S— or —CH$_2$—,
$Y^2$ represents —NR$^9$— or —CH$_2$—,
m is 0 or 1,
n is 0, 1 or 2,
p is 0 or 1,
R denotes hydrogen,
- an optionally substituted aliphatic radical having 1–21 carbon atoms,
- an optionally substituted alicyclic radical having 3–20 carbon atoms,
- an optionally substituted aromatic radical having 6–12 carbon atoms,
- an optionally substituted araliphatic radical having 7–32 carbon atoms,
- an optionally substituted alicyclic-aliphatic radical having 4–20 carbon atoms,
- an optionally substituted heteroaromatic or heteroaromatic-(C$_1$-C$_8$)-aliphatic radical having 5–12 ring atoms, or
- a radical OR$^a$ or SR$^a$, in which $R^a$ represents an optionally substituted aliphatic radical having 1–4 carbon atoms, an optionally substituted aromatic radical having 6–12 carbon atoms, or an optionally substituted heteroaromatic radical having 5–12 ring atoms, $R^1$ denotes hydrogen,
- an optionally substituted aliphatic radical having 1–21 carbon atoms,
- an optionally substituted alicyclic radical having 3–20 carbon atoms,
- an optionally substituted alicyclic-aliphatic radical having 4–20 carbon atoms,
- an optionally substituted aromatic radical having 6–12 carbon atoms,
- an optionally substituted araliphatic radical having 7–32 carbon atoms,
- an optionally substituted heteroaromatic or heteroaromatic-(C$_1$-C$_8$)-aliphatic radical having 5–12 ring atoms, or, if not already covered by the above definitions, the side-chain, protected where necessary, of a naturally occurring α-amino acid, $R^2$ and $R^3$ are identical or different and denote hydrogen, an optionally substituted aliphatic radical having 1–21 carbon atoms,
- an optionally substituted alicyclic radical having 3–20 carbon atoms,
- an optionally substituted aromatic radical having 6–12 carbon atoms,
- an optionally substituted araliphatic radical having 7–32 carbon atoms, $R^4$ represents hydrogen or (C$_1$-C$_6$)-alkyl and
$R^5$ represents (C$_1$-C$_6$)-alkyl, (C$_3$-C$_6$)-cycloalkyl or or $R^4$ and $R^5$ form, together with the atoms carrying them, a mono-, bi- or tricyclic, heterocyclic ring system having 3 to 15 ring carbon atoms,
$R^6$ denotes hydrogen, amino, (C$_1$-C$_6$)-alkyl, (C$_6$-C$_{12}$)-aryl or (C$_7$-C$_{13}$)-aralkyl,
$R^7$ denotes (C$_1$-C$_6$)-alkyl or (C$_7$-C$_{13}$)-aralkyl, preferably —(CH$_2$)$_4$—C$_6$H$_5$,
$R^8$ denotes (C$_1$-C$_6$)-alkyl, which is optionally monosubstituted by (C$_1$-C$_6$)-alkanoyloxy, preferably 2-methyl-1-propionyloxypropyl, and
$R^9$ denotes hydrogen or (C$_1$-C$_6$)-alkyl; such as compounds of the formula II, $$R^3OOC-\overset{*}{C}H-N-\overset{*}{C}-\overset{*}{C}H-NH-\overset{*}{C}H-(CH_2)_n-R \qquad (II)$$
$$\qquad\;\; | \quad\; | \;\; || \;\; | \qquad\qquad\; |$$
$$\qquad\;\; R^4 \;\; R^5 \;\; O \;\; R^1 \qquad\qquad COOR^2$$

in which
n is 1 or 2,
R denotes hydrogen,
- an optionally substituted aliphatic radical having 1–21 carbon atoms, an optionally substituted alicyclic radical having 3–20 carbon atoms, an optionally substituted aromatic radical having 6–12 carbon atoms, an optionally substituted araliphatic radical having 7–32 carbon atoms, an optionally substituted alicyclic-aliphatic radical having 4–20 carbon atoms, an optionally substituted heteroaromatic or heteroaromatic-($C_1$–$C_8$)-aliphatic radical having 5–12 ring atoms, or a radical $OR^a$ or $SR^a$, in which $R^a$ represents an optionally substituted aliphatic radical having 1–4 carbon atoms, an optionally substituted aromatic radical having 6–12 carbon atoms, or an optionally substituted heteroaromatic radical having 5–12 ring atoms, $R^1$ denotes hydrogen, an optionally substituted aliphatic radical having 1–21 carbon atoms, an optionally substituted alicyclic radical having 3–20 carbon atoms, an optionally substituted alicyclic-aliphatic radical having 4–20 carbon atoms, an optionally substituted aromatic radical having 6–12 carbon atoms, an optionally substituted araliphatic radical having 7–32 carbon atoms, an optionally substituted heteroaromatic or heteroaromatic-($C_1$–$C_8$)-aliphatic radical having 5–12 ring atoms, or, if not already covered by the above definitions, the side-chain, protected where necessary, of a naturally occurring α-amino acid, $R^2$ and $R^3$ are identical or different and denote hydrogen, an optionally substituted aliphatic radical having 1–21 carbon atoms, an optionally substituted alicyclic radical having 3–20 carbon atoms, an optionally substituted aromatic radical having 6–12 carbon atoms, an optionally substituted araliphatic radical having 7–32 carbon atoms, and $R^4$ and $R^5$ form, together with the atoms carrying them, a mono-, bi- or tricyclic heterocyclic ring system having 3 to 15 ring carbon atoms.

An optionally substituted aliphatic radical is understood to be an aliphatic acyclic radical, i.e. a radical with an open, straight or branched carbon chain such as, for example, alkyl, alkenyl, alkynyl and corresponding multiply unsaturated radicals. It is preferably unsubstituted or, as described below, for example, for carboxyl, carbamoyl, aminoalkyl, alkanoylaminoalkyl, alkoxycarbonylaminoalkyl, arylalkoxycarbonylaminoalkyl, arylalkylaminoalkyl, alkylaminoalkyl, dialkylaminoalkyl, alkylthioalkyl, arylthioalkyl, carboxyalkyl, carbamoylalkyl, alkoxycarbonylalkyl, alkanoyloxyalkyl, alkoxycarbonyloxyalkyl, aroyloxyalkyl or aryloxycarbonyloxyalkyl, monosubstituted.

An optionally substituted alicyclic radical, and the corresponding optionally substituted alicyclic-aliphatic radical which is linked via an open carbon chain, is a preferably mono- to pentacyclic, isocyclic, nonaromatic radical which has single bonds or asymmetrically distributed double bonds and can also be branched (i.e. carry open-chain aliphatic side-chains) and is linked via a ring carbon atom or a side-chain carbon atom. It is preferably unsubstituted. When several rings are components of a radical of this type, they are fused, spirolinked or isolated. Examples of radicals of this type are cycloalkyl, cycloalkenyl, cycloalkylalkyl, bicycloalkyl, tricycloalkyl and radicals derived from mono-, bi- or oligocyclic terpenes such as menthyl, isomenthyl, bornanyl, bornyl, caranyl, epibornyl, epiisobornyl, isobornyl, menthanyl, neomenthyl, neoisomenthyl, pinanyl and thujanyl; they are preferably unsubstituted (according to the present definition, aliphatic side-chains are not substituents).

An optionally substituted aromatic radical is preferably aryl such as phenyl, biphenylyl or naphthyl, which is optionally mono-, di- or trisubstituted as indicated below for aryl. Radicals derived from aryl, such as aralkyl, aryloxy, arylthio or aroyl, preferably benzoyl, can be substituted as for aryl.

An optionally substituted heteroaromatic radical is preferably an aromatic mono- or bicyclic heterocyclic radical having 5 to 7 or 8 to 12, preferably up to 10, ring atoms respectively, 1 or 2 of these ring atoms representing sulfur or oxygen atoms and/or 1 to 4 of these ring atoms representing nitrogen atoms, and is understood to be, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated. A heteroaromatic radical and the corresponding heteroaromaticaliphatic radical can be substituted as defined below.

An optionally substituted araliphatic radical is understood to be, in particular, aralkyl radicals such as arylalkyl, diarylalkyl, indanyl or fluorenyl, in which aryl is as defined above and which can be substituted in the manner indicated there.

$R^4$ and $R^5$ can form, with the atoms carrying them, a mono-, bi- or tricyclic heterocyclic ring system which has 3 to 15 ring carbon atoms and preferably has up to 2 sulfur atoms and up to 2 nitrogen atoms in the ring, in particular up to 1 sulfur atom.

Particularly suitable ring systems of these types are those of the following group:

Pyrrolidine (O); thiazolidine (R); tetrahydroisoquinoline (A); decahydroisoquinoline (B); octahydroindole (C); indoline (Q); octahydrocyclopenta[b]pyrrole (D); 2-azaspiro[4.5]decane (E); 2-azaspiro[4.4]nonane (F); spiro[(bicyclo[2.2.1]heptane)-2,3'-pyrrolidine] (G); spiro[(bicyclo[2.2.2]octane)-2,3'-pyrrolidine] (H); 2-azatricyclo[4.3.0.1$^{6,9}$]decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); 1,2,3,3a,4,6a-hexahydrocyclopenta[b]pyrrole (P), all of which can optionally be substituted. Pyrrolidine (O) and thiazolidine (R); can be monosubstituted by, for example, ($C_6$–$C_{12}$)-aryl, (phenyl, 2-hydroxyphenyl etc.), ($C_6$–$C_{12}$)-arylmercapto (such as phenylmercapto) or ($C_3$–$C_7$)-cycloalkyl (such as cyclohexyl). Tetrahydroisoquinoline (A) can carry, for example, in the aryl moiety, up to 2 ($C_1$–$C_6$)-alkoxy radicals, preferably methoxy radicals. A corresponding statement applies to the other ring systems. However, the unsubstituted systems are preferred.

With compounds of the formula I or II which have several chiral atoms all possible diastereomers, as racemates or enantiomers, or mixtures of various diastereomers are suitable.

The suitable heterocyclic ring systems have the following structural formulae.
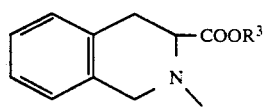 A
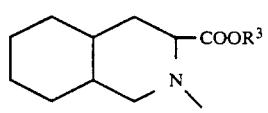 B
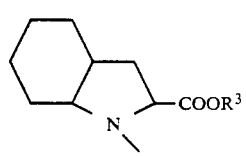 C
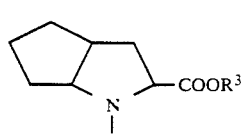 D
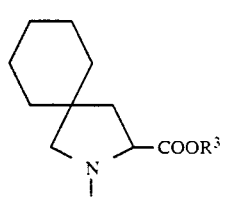 E
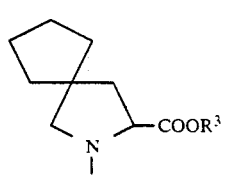 F
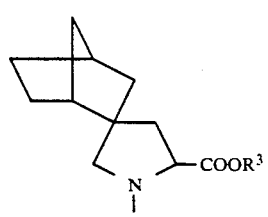 G
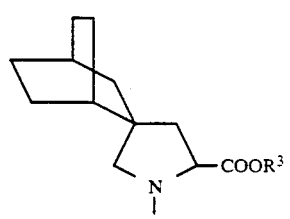 H
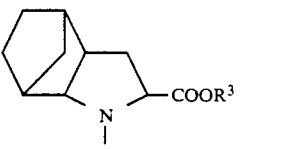 I
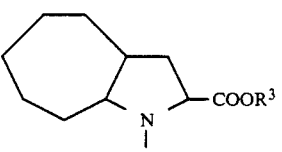 J
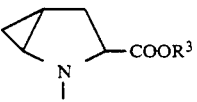 K
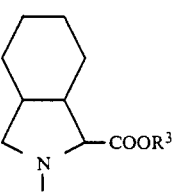 L
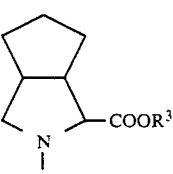 M
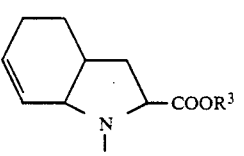 N
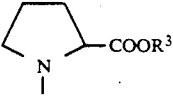 O
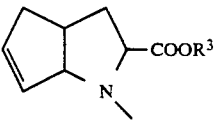 P
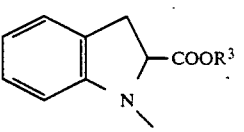 Q

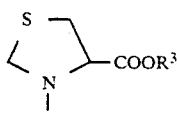

A preferred embodiment comprises use of compounds of the formula I, preferably those of the formula II, in which a) n is 1 or 2;
b) R
  1. denotes hydrogen;
  2. denotes alkyl having 1-18 carbon atoms;
  3. denotes an aliphatic acyclic radical of the formula $C_aH_{(2a-b+1)}$, in which double bonds, if their number exceeds 1, are not cumulative, a represents an integer 2 to 18, and b represents an nteger 2 to a;
  4. denotes a mono-, di-, tri-, tetra- or pentacyclic, non-aromatic hydrocarbon radical of the formula $C_cH_{(2c-d-1)}$, which is optionally branched, in which c represents an integer 3 to 20, and d represents an even number 0 to (c−2);
  5. denotes aryl which has 6-12 carbon atoms and can be mono-, di- or trisubstituted by $(C_1-C_8)$-alkyl, $(C_1-C_4)$-alkoxy, hydroxyl, -halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl;
  6. if n is 2, denotes $(C_6-C_{12})$-aryl-$(C_1-C_8)$-alkyl or di-$(C_6-C_{12})$-aryl-$(C_1-C_8)$-alkyl, each of which can be substituted in the aryl moiety as described under I.b)5; or
  7. alkoxy having 1-4 carbon atoms;
  8. aryloxy which has 6-12 carbon atoms and can be substituted as described under I.b)5;
  9. mono- or bicyclic heteroaryloxy or heteroaryl-$(C_1-C_8)$-alkyl which has 5-7 or 8-10 ring atoms respectively, up to 9 of these ring atoms representing carbon and 1 to 2 ring atoms representing sulfur or oxygen and/or 1 to 4 ring atoms representing nitrogen, and which can be substituted in the heteroaryl as described under I.b)5;
  10. amino-$(C_1-C_8)$-alkyl;
  11. $(C_1-C_4)$-alkanoylamino-$(C_1-C_8)$-alkyl;
  12. $(C_7-C_{13})$-aroylamino-$(C_1-C_8)$-alkyl;
  13. $(C_1-C_4)$-alkoxycarbonylamino-$(C_1-C_8)$-alkyl;
  14. $(C_6-C_{12})$-aryl-$(C_1-C_4)$-alkoxycarbonylamino-$(C_1-C_8)$-alkyl;
  15. $(C_6-C_{12})$-aryl-$(C_1-C_4)$-alkylamino-$(C_1-C_8)$alkyl;
  16. $(C_1-C_4)$-alkylamino-$(C_1-C_8)$-alkyl;
  17. di-$(C_1-C_4)$-alkylamino-$(C_1-C_8)$-alkyl;
  18. guanidino-$(C_1-C_8)$-alkyl,
  19. imidazolyl;
  20. indolyl;
  21. $(C_1-C_4)$-alkylthio;
  22. if n is 2, $(C_1-C_4)$-alkylthio-$(C_1-C_8)$-alkyl;
  23. $(C_6-C_{12})$-arylthio-$(C_1-C_8)$-alkyl which can be substituted in the aryl moiety as described under I.b)5;
  24. $(C_6-C_{12})$-aryl-$(C_1-C_8)$-alkylthio which can be substituted in the aryl moiety as described under I.b)5;
  25. if n is 2, carboxy-$(C_1-C_8)$-alkyl;
  26. carboxyl;
  27. carbamoyl;
  28. if n is 2, carbamoyl-$(C_1-C_8)$-alkyl;
  29. $(C_1-C_4)$-alkoxy-carbonyl-$(C_1-C_8)$-alkyl;
  30. if n is 2, $(C_6-C_{12})$-aryloxy-$(C_1-C_8)$-alkyl which can be substituted in the aryl moiety as described under I.b)5; or
  31. denotes $(C_6-C_{12})$-aryl-$(C_1-C_8)$-alkoxy which can be substituted in the aryl moiety as described under I.b)5;
c) $R^1$
  1. denotes hydrogen;
  2. denotes alkyl having 1-18 carbon atoms;
  3. denotes an aliphatic radical of the formula $C_aH_{(2a-b+1)}$, in which double bonds, if their number exceeds 1, are not cumulative, a represents an integer 2 to 18, and b represents an even number 2 to a;
  4. denotes a mono-, di-, tri-, tetra- or pentacyclic, non-aromatic hydrocarbon radical of the formula $C_cH_{(2c-d-1)}$, which is optionally branched and in which c represents an integer 3 to 20 and d represents an even number 0 to (c−2);
  5. aryl which has 6-12 carbon atoms and can be substituted as described under I.b)5;
  6. $(C_6-C_{12})$-aryl-$(C_1-C_8)$-alkyl or $(C_7-C_{13})$-aroyl-$(C_1-C_8)$-alkyl, both of which can be substituted as described for aryl under I.b)5;
  7. mono- or bicyclic, optionally partially hydrogenated, heteroaryl or heteroaryl-$(C_1-C_8)$-alkyl which has 5-7 or 8-10 ring atoms respectively, up to 9 of these ring atoms representing carbon and 1 or 2 ring atoms representing sulfur or oxygen and/or 1 to 4 ring atoms representing nitrogen, and which can be substituted in the heteroaryl as described for aryl under I.b)5; or
  8. if not already covered by c) 1.-8., the optionally protected side-chain of a naturally occurring α-amino acid of the formuLa $R^1$—CH(NH-2)—COOH;
d) $R^2$ and $R^3$ are identical or different and
  1. denote hydrogen;
  2. alkyl having 1-18 carbon atoms;
  3. denote an aliphatic acyclic radical of the formula $C_aH_{(2a-b+1)}$, in which double bonds, if their number exceeds 1, are not cumulative, a represents an integer 2 to 18, and b represents an even number 2 to a;
  4. a mono-, di-, tri-, tetra- or pentacyclic, nonaromatic hydrocarbon radical of the formula $C_cH_{(2c-d-1)}$, which is optionally branched and in which c represents an integer 3 to 20 and d represents an even number 0 to (c−2);
  5. di-$(C_1-C_4)$-alkylamino-$(C_1-C_8)$-alkyl;
  6. $(C_1-C_5)$-alkanoyloxy-$(C_1-C_8)$-alkyl;
  7. $(C_1-C_6)$-alkoxy-carbonyloxy-$(C_1-C_8)$-alkyl;
  8. $(C_7-C_{13})$-aroyloxy-$(C_1-C_8)$-alkyl;
  9. $(C_6-C_{12})$-aryloxycarbonyloxy-$(C_1-C_8)$-alkyl;
  10. aryl having 6-12 carbon atoms; or
  11. denote $(C_7-C_{20})$-aralkyl; it being possible for the radicals mentioned under d) 8., 9., 10. and 11. to be substituted in the aryl moiety as described under I.b)5; and
e) $R^4$ and $R^5$ form, together with the atoms carrying them, a mono-, bi- or tricyclic heterocyclic ring system having 3 to 15 ring carbon atoms.

A particularly preferred embodiment comprises use of compounds of the formula I, preferably those of the formula II,
in which
n is 1 or 2,
R denotes hydrogen,
  alkyl having 1–8 carbon atoms,
  alkenyl having 2–6 carbon atoms,
  cycloalkyl having 3–9 carbon atoms,
  aryl which has 6–12 carbon atoms and can be mono-, di- or trisubstituted by $(C_1-C_4)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl,
  alkoxy having 1–4 carbon atoms,
  aryloxy which has 6–12 carbon atoms and can be substituted as described above for aryl,
  mono- or bicyclic heteroaryloxy which has 5–7 or 8–10 ring atoms respectively, 1 to 2 of these ring atoms representing sulfur or oxygen atoms, and/or 1 to 4 of these ring atoms representing nitrogen, and which can be substituted as described above for aryl, amino-$(C_1-C_4)$-alkyl, $(C_1-C_4)$-alkanoylamino-$(C_1-C_4)$alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino$(C_1-C_4)$-alkyl, $(C_6-C_{12})$-aryl-$(C_1-C_4)$-alkylamino-$(C_1-C_4)$-alkyl, $(C_1-C_4)$-alkylamino-$(C_1-C_4)$-alkyl, di-$(C_1-C_4)$-alkylamino-$(C_1-C_4)$-alkyl, guanidino-$(C_1-C_4)$-alkyl, imidazolyl, indolyl, $(C_1-C_4)$-alkylthio, $(C_1-C_4)$-alkylthio-$(C_1-C_4)$-alkyl,
  $(C_6-C_{12})$-arylthio-$(C_1-C_4)$-alkyl which can be substituted in the aryl moiety as described above for aryl,
  $(C_6-C_{12})$-aryl-$(C_1-C_4)$-alkylthio which can be substituted in the aryl moiety as described above for aryl, carboxy-$(C_1-C_4)$-alkyl, carboxyl, carbamoyl, carbamoyl-$(C_1-C_4)$-alkyl, $(C_1-C_4)$-alkoxycarbonyl-$(C_1-C_4)$-alkyl,
  $(C_6-C_{12})$-aryloxy-$(C_1-C_4)$-alkyl which can be substituted in the aryl moiety as described above for aryl, or
  $(C_6-C_{12})$-aryl-$(C_1-C_4)$-alkoxy which can be substituted in the aryl moiety as described above for aryl,
$R^1$ denotes hydrogen,
  alkyl having 1–6 carbon atoms,
  alkenyl having 2–6 carbon atoms,
  alkynyl having 2–6 carbon atoms,
  cycloalkyl having 3–9 carbon atoms,
  cycloalkenyl having 5–9 carbon atoms, $(C_3-C_9)$-cycloalkyl-$(C_1-C_4)$-alkyl, $(C_5-C_9)$-cycloalkenyl-$(C_1-C_4)$-alkyl,
  optionally partially hydrogenated aryl which has 6–12 carbon atoms and can be substituted as described above for R, $(C_6-C_{12})$-aryl-$(C_1-C_4)$-alkyl or $(C_7-C_{13})$, aroyl-$(C_1$ or $C_2)$-alkyl, both of which can be substituted as for the preceding aryl, mono- or bicyclic, optionally partially hydrogenated heteroaryl which has 5–7 or 8–10 ring atoms respectively, 1 to 2 of these ring atoms representing sulfur or oxygen atoms, and/or 1 to 4 of these ring atoms representing nitrogen atoms, and which can be substituted as for the preceding aryl, or
  the optionally protected side-chain of a naturally occurring α-amino acid, $R^1$—CH(NH$_2$)—COOH,
$R^2$ and $R^3$ are identical or different and denote hydrogen,
  alkyl having 1–6 carbon atoms,
  alkenyl having 2–6 carbon atoms, di-$(C_1-C_4)$-alkylamino-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl,
  aryl having 6–12 carbon atoms, $(C_6-C_{12})$-aryl-$(C_1-C_4)$-alkyl, $(C_3-C_9)$-cycloalkyl or $(C_3-C_9)$-cycloalkyl-$(C_1-C_4)$-alkyl, and
$R^4$ and $R^5$ have the abovementioned meaning, particularly such compounds in which
n is 1 or 2,
R denotes $(C_1-C_6)$-alkyl, $(C_1-C_6)$-alkenyl, $(C_1-C_9)$-cycloalkyl, amino-$(C_1-C_4)$-alkyl, $(C_2-C_5)$-acylamino-$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or 3-indolyl, in particular methyl, ethyl, cyclohexyl, tert.-butoxycarbonylamino-$(C_1-C_4n)$-alkyl, benzoyloxycarbonylamino-$(C_1-C_4)$-alkyl, or phenyl which can be mono- or disubstituted, or in the case of methoxy trisubstituted, by phenyl, $(C_1-C_2)$-alkyl, $(C_1$ or $C_2)$-alkoxy, hydroxyl, fluorine, chlorine, bromine, amino, $(C_1-C_4)$-alkylamino, di-$(C_1-C_4)$-alkylamino, nitro and/or methylenedioxy,
$R^1$ denotes hydrogen or $(C_1-C_6)$-alkyl which can optionally be substituted by amino, $(C_1-C_6)$-acylamino or benzoylamino, or $(C_2-C_6)$-alkenyl, $(C_3-C_9)$-cycloalkyl, $(C_5-C_9)$-cycloalkenyl, $(C_3-C_7)$-cycloalkyl-$(C_1-C_4)$-alkyl, $(C_6-C_{12})$-aryl or partially hydrogenated aryl, each of which can be substituted by $(C_1-C_4)$-alkyl, $(C_1$ or $C_2)$-alkoxy or halogen, or $(C_6-C_{12})$-aryl-$(C_1$ to $C_4)$-alkyl or $(C_7-C_{13})$-aroyl$(C_1-C_2)$-alkyl, both of which can be substituted in the aryl radical as defined previously, a mono- or bicyclic heterocyclic radical having 5 to 7 or 8 to 10 ring atoms respectively, 1 to 2 of these ring atoms representing sulfur or oxygen atoms, and/or 1 to 4 of these ring atoms representing nitrogen atoms, or a side-chain of a naturally occurring, optionally protected α-amino acid, but in particular hydrogen, $(C_1-C_3)$-alkyl, $(C_2$ or $C_3)$-alkenyl, the optionally protected side-chain of lysine, benzyl, 4-methoxybenzyl, 4-ethoxybenzyl, phenethyl, 4-aminobutyl or benzoylmethyl,
$R^2$ and $R^3$ denote identical or different radicals hydrogen, $(C_1-C_6)$-alkyl, $(C_2-C_6)$-alkenyl or $(C_6-C_{12})$-aryl-$(C_1-C_4)$-alkyl, but in particular hydrogen, $(C_1-C_4)$-alkyl or benzyl, and
$R^4$ and $R^5$ have the abovementioned meaning.
If $R^1$ represents a side-chain of a protected naturally occurring α-amino acid, such as, for example, protected Ser, Thr, Asp, Asn, Glu, Gln, Arg, Lys, Hyl, Cys, Orn, Cit, Tyr, Trp or His, preferred protective groups are the groups customary in peptide chemistry (cf. Houben-Weyl, vol. XV/1 and XV/2). In the case where $R^1$ denotes the protected side-chain of lysine, the known amino protective groups are preferred, but in particular Z, Boc or (C$_1$-C$_6$)-alkanoyl. Suitable and preferred O-protective groups for tyrosine are (C$_1$-C$_6$)-alkyl, in particular methyl or ethyl.

It is possible and particularly advantageous to use the following compounds according to the invention:

2-[N-(1-S-carbethoxy-3-phenylpropyl)-S-alanyl]-S-1,2,3,4-tetrahydroisoquinoline-3-carboxylic acid 2-[N-(1-S-carbethoxy-3-cyclohexylpropyl)-S-alanyl]-S-1,2,3,4-tetrahydroisoquinoline-3-carboxylic acid 2-[N-(1-S-carbethoxy-3-phenylpropyl)-S-lysyl]-S-1,2,3,4-tetrahydroisoquinoline-3-carboxylic acid 2-[N-(1-S-carbethoxy-3-phenylpropyl)-O-ethyl-S-tyrosyl]-S-1,2,3,4-tetrahydroisoquinoline-3-carboxylic acid 2-[N-(1-S-carbethoxy-3-phenylpropyl)-S-alanyl]-(3S)-decahydroisoquinoline-3-carboxylic acid 1-[N-(1-S-carbethoxy-3-phenylpropyl)-S-alanyl]-(2S,3aS,7aS)-octahydroindole-2-carboxylic acid 1-[N-(1-S-carbethoxy-3-cyclohexylpropyl)-S-alanyl]-(2S,3aS,7aS)-octahydroindole-2-carboxylic acid 1-[N-(1-S-carbethoxy-3-phenylpropyl)-S-lysyl]-(2S,3aS,7aS)-octahydroindole-2-carboxylic acid 1-[N-(1-S-carbethoxy-3-cyclohexylpropyl)-S-lysyl]-(2S,3aS,7aS)-octahydroindole-2-carboxylic acid 1-[N-(1-S-carbethoxy-3-cyclohexylpropyl)-S-lysyl]-(2s,3aS,7aS)-octahydroindole-2-carboxylic acid 1-[N-(1-S-carbethoxy-3-phenylpropyl)-O-methyl-S-tyrosyl]-(2S,3aS,7aS)-octahydroindole-2-carboxylic acid 1-[N-(1-S-carbethoxy-3-phenylpropyl)-O-ethyl-S-tyrosyl]-(2S,3aS,7aS)-octahydroindole-2-carboxylic acid 1-[N-(1-S-carbethoxy-3-(3,4-dimethylphenylpropyl)-S-alanyl]-(2S,3aS,7aS)-octahydroindole-2-carboxylic acid 1-[N-[1-S-carbethoxy-3-(4-fluorophenyl)-propyl]-S-alanyl]-(2S,3aS,7aS)-octahydroindole-2-carboxylic acid 1-[N-[1-S-carbethoxy-3-(4-methoxyphenyl)-propyl]-S-alanyl]-(2S,3aS,7aS)-octahydroindole-2-carboxylic acid 1-[N-[1-S-carbethoxy-3-(3,4-dimethoxyphenyl)-propyl]-S-alanyl] -(2S,3aS,7aS)-octahydroindole-2-carboxylic acid 1-[N-(1-S-carbethoxy-3-cyclopentylpropyl)-S-alanyl]-(2S,3aS,7aS)-octahydroindole-2-carboxylic acid 1-[N-(1-S-carbethoxy-3-phenylpropyl)-S-alanyl]-(2S,3aR,7aS)-octahydroindole-2-carboxylic acid 1-[N-(1-S-carbethoxy-3-cyclohexylpropyl)-S-alanyl]-(2S,3aR,7aS)-octahydroindole-carboxylic acid 1-[N-(1-S-carbethoxy-3-phenylpropyl)-S-lysyl]-(2S,3aR,7aS)-octahydroindole-2-carboxylic acid 1-[N-(1-S-carbethoxy-3-cyclohexyl ropyl)-S-lysyl]-(2S,3aR,7aS)-octahydroindole-2-carboxylic acid 1-[N-(1-S-carbethoxy-3-phenylpropyl)-O-ethyl-S-tyrosyl]-(2S,3aS,7aR)-octahydroindole-2-carboxylic acid 1-[N-(1-S-carbethoxy-3-phenylpropyl)-S-alanyl]-(2S,3aR,7aR)-octahydroindole-2-carboxylic acid 1-[N-(1-S-carbethoxy-3-phenylpropyl)-S-lysyl]-(2S,3aS,7aS)-octahydroindole-2-carboxylic acid 1-[N-(1-S-carbethoxy-3-cyclohexylpropyl)-S-alanyl]-(2S,3aR,7aR)-octahydroindole-2-carboxylic acid 1-[N-(1-S-carbethoxy-3-cyclohexylpropyl)-O-ethyl-S-tyrosyl]-(2S,3aR,7aR)-octahydroindole-2-carboxylic acid 1-[N-(1-S-carbethoxy-3-phenylpropyl)-S-alanyl]-(2S,3aS,7aR)-octahydroindole-2-carboxylic acid 1-[N-(1-S-carbethoxy-3-phenylpropyl)-O-ethyl-S-tyrosyl]-(2S,3aS,7aS)-octahydroindole-2-carboxylic acid 1-[N-(1-S-carbethoxy-3,4-dimethylphenylpropyl)-S-alanyl]-(2S,3aS,7aS)-octahydroindole-2-carboxylic acid 1-[N-[1-S-carbethoxy-3-(4-fluorophenyl)-propyl]-S-alanyl]-(2S,3aS,7aS)-octahydroindole-2-carboxylic acid 1-[N-[1-S-carbethoxy-3-(4-methoxyphenyl)-propyl]-S-alanyl]-(2S,3aS,7aS)-octahydroindole-2-carboxylic acid 1-[N-[1-S-carbethoxy-3-(3,4-dimethoxyphenyl)-propyl]-S-alanyl]-(2S,3aS,7aS)-octahydroindole-2-carboxylic acid 1-[N-(1-S-carbethoxy-3-cyclopentylpropyl)-S-alanyl]-(2S,3aS,7aS)-octahydroindole-2-carboxylic acid 2-[N-(1-S-carbethoxy-3-phenylpropyl)-S-alanyl]-cis-endo-2-azabicyclo[3.3.0]octane-3-S-carboxylic acid 2-[N-(1-S-carbethoxy-3-phenylpropyl)-S-lysyl]-cis-endo- 2-azabicyclo[3.3.0]octane-3-S-carboxylic acid 2-[N-(1-S-carbethoxy-3-cyclohexylpropyl)-S-alanyl]-cis-endo-2-azabicyclo[3.3.0]octane-3-S-carboxylic acid 2-[N-(1-S-carboxy-3-cyclohexylpropyl)-S-alanyl]-cis-endo-2-azabicyclo[3.3.0]octane-3-S-carboxylic acid 2-[N-(1-S-carbethoxy-butyl)-S-alanyl]-cis-endo-2-azabicyclo[3.3.0]octane-3-S-carboxylic acid 2-[N-(1-S-carbethoxy-3-(3,4-dimethoxyphenylpropyl)-S-alanyl]-cis-endo-2-azabicyclo[3.3.0]octane-3-S-carboxylic acid 2-[N-(1-S-carbethoxy-3-cyclopentylpropyl)-S-alanyl]-cis-endo-azabicyclo-[3.3.0]octane-3-S-carboxylic acid 2-[N-(1-S-carbethoxy-3-phenylpropyl)-O-methyl-S-tyrosyl]-cis-endo-2-azabicyclo[3.3.0]octane-3-S-carboxylic acid 2-[N-(1-S-carbethoxy-3-phenylpropyl)-O-ethyl-S-tyrosyl]-cis-endo-2-azabicyclo[3.3.0]octane-3-S-carboxylic acid 2-[N-(1-S-carbethoxy-3-(4-fluorophenylpropyl)-S-alanyl]-cis-endo-2-azabicyclo[3.3.0]octane-3-S-carboxylic acid 2-[N-(1-S-carbethoxy-3-(4-methoxyphenylpropyl)-S-alanyl]-cis-endo-2-azabicyclo[3.3.0]octane-3-S-carboxylic acid 1-[N-(1-S-carbethoxy-3-phenylpropyl)-S-lysyl]-(2S,3aR,6aS)-octahydrocyclopenta[b]pyrrole-2-carboxylic acid 1-[N-(1-S-carbethoxy-3-cyclohexylpropyl)-lysyl]-(2S,3aR,6aS)-octahydrocyclopenta[b]pyrrole-2-carboxylic acid 1-[N-(1-S-carbethoxy-3-phenylpropyl)-O-ethyl-S-tyrosyl]-(2S,3aR,6aS)-octahydrocyclopenta[b]pyrrole-2-carboxylic acid 1-[N-(1-S-carbethoxy-3-phenylpropyl)-S-alanyl]-2-(2S,3aR,6aS)-octahydrocyclopenta[b]pyrrole-2-carboxylic acid 2-[N-(1-S-carbethoxy-3-phenylpropyl)-S-alanyl]-2-azaspiro-[4.5]decane-3-S-carboxylic acid 2-[N-(1-S-carbethoxy-3-phenylpropyl)-O-ethyl-2-tyrosyl]-2-azaspiro-[4.5]decane-3-S-carboxylic acid 2-[N-(1-S-carbethoxy-3-phenylpropyl)-S-lysyl]-2-azaspiro4.5]decane-3-S-carboxylic acid 2-[N-(1-S-carbethoxy-3-cyclohexylpropyl)-S-alanyl]-2-azaspiro[4.5]decane-3-S-carboxylic acid 2-[N-(1-S-carbethoxy-3-cyclohexylpropyl)-S-lysyl]-2-azaspiro[4.5]decane-3-S-carboxylic acid 2-[N-(1-S-carbethoxy-3-phenylpropyl)-S-alanyl]-2-azaspiro[4.4]nonane-3-S-carboxylic acid
2-[N-(1-S-carbethoxy-3-phenylpropyl)-O-ethyl-S-tyrosyl]-2-azaspiro[4.4]nonane-3-S-carboxylic acid
2-[N-(1-S-carbethoxy-3-phenylpropyl)-S-lysyl]-2-azaspiro[4.4]nonane-3-S-carboxylic acid
2-[N-(1-S-carbethoxy-3-cyclohexylpropyl)-S-alanyl]-2-azaspiro[4.4]nonane-3-S-carboxylic acid
2-[N-(1-S-carbethoxy-3-cyclopentylpropyl)-S-alanyl]-2-azaspiro[4.4]nonane-3-S-carboxylic acid
2-[N-(1-S-carbethoxy-3-cyclopentylpropyl)-S-lysyl]-2-azaspiro[4.4]nonane-3-S-carboxylic acid
1'-[N-(1-S-carbethoxy-3-phenylpropyl)-S-alanyl]-spiro[bicyclo[2.2.1]heptane-2,3'-pyrrolidine]-5'-S-carboxylic acid
1'-[N-(1-S-carbethoxy-3-phenylpropyl)-O-ethyl-S-tyrosyl]-spiro[bicyclo[2.2.1]heptane-2,3'-pyrrolidine]-5'-S-carboxylic acid
1'-[N-(1-S-carbethoxy-3-phenylpropyl)-S-lysyl]-spiro[bicyclo[2.2.1]heptane-2,3'-pyrrolidine]-5'-S-carboxylic acid
1'-[N-(1-S-carbethoxy-3-cyclohexylpropyl)-S-alanyl]-spiro[bicyclo[2.2.1]heptane-2,3'-pyrrolidine]5'-S-carboxylic acid
1'-[N-(1-S-carbethoxy-3-cyclohexylpropyl)-S-lysyl]-spiro[bicyclo[2.2.1]heptane-2,3'-pyrrolidine]-5'-S-carboxylic acid
1'-[N-(1-S-carbethoxy-3-phenylpropyl)-S-alanyl]-spiro[bicyclo[2.2.2]octane-2,3'-pyrrolidine]-5'-S-carboxylic acid
1'-[N-(1-S-carbethoxy-3-phenylpropyl)-O-ethyl-tyrosyl]-spiro-[bicyclo[2.2.2]octane-2,3'-pyrrolidine]-5'-S-carboxylic acid
1'-[N-(1-S-carbethoxy-3-phenylpropyl)-S-lysyl]-spiro[bicyclo[2.2.2]octane-2,3'-pyrrolidine]-5'-S-carboxylic acid
1'-[N-(1-S-carbethoxy-3-cyclohexylpropyl)-S-alanyl]-spiro[bicyclo[2.2.2]octane-2,3'-pyrrolidine]-5'-S-carboxylic acid
2-[N-(1-S-carbethoxy-3-phenylpropyl)-S-alanyl]-2-azatricyclo[4.3.0.1$^{6,9}$]decane-3-S-carboxylic acid
2-[N-(1-S-carbethoxy-3-phenylpropyl)-O-ethyl-S-tyrosyl]-2-azatricyclo[4.3.0.1$^{6,9}$]decane-3-S-carboxylic acid
2-[N-(1-S-carbethoxy-3-phenylpropyl)-S-lysyl]-2-azatricyclo[4.3.0.1$^{6,9}$]decane-3-S-carboxylic acid
2-[N-(1-S-carbethoxy-3-cyclohexylpropyl)-S-alanyl]-2-azatricyclo[4.3.0.1$^{6,9}$]decane-3-S-carboxylic acid
2-[N-(1-S-carbethoxy-3-cyclohexylpropyl)-S-lysyl]-2-azatricyclo[4.3.0.1$^{6,9}$]decane-3-S-carboxylic acid
1-[N-(1-S-carbethoxy-3-phenylpropyl)-S-alanyl]-decahydrocyclohepta[b]pyrrole-2-S-carboxylic acid
1-[N-(1-S-carbethoxy-3-phenylpropyl)-O-ethyl-S-tyrosyl]-decahydrocyclohepta[b]pyrrole-2-S-carboxylic acid
1-[N-(1-S-carbethoxy-3-phenylpropyl)-S-lysyl]-decahydrocyclohepta[b]pyrrole-2-S-carboxylic acid
1-[N-(1-S-carbethoxy-3-cyclohexylpropyl)-S-alanyl]-decahydrocyclohepta[b]pyrrole-2-S-carboxylic acid
1-[N-(1-S-carbethoxy-3-cyclohexylpropyl)-S-lysyl]-decahydrocyclohepta[b]pyrrole-2-S-carboxylic acid
2-[N-(1-S-carbethoxy-3-phenylpropyl)-S-alanyl]-trans-octahydroisoindole-1-S-carboxylic acid
2-[N-(1-S-carbethoxy-3-phenylpropyl)-S-alanyl]-cis-octahydroisoindole-1-S-carboxylic acid
2-[N-(1-S-carbethoxy-3-cyclohexylpropyl)-S-alanyl]-transoctahydroisoindole-1-S-carboxylic acid
2-[N-(1-S-carbethoxy-3-cyclohexylpropyl)-S-alanyl]-cis-octahydroisoindole-1-S-carboxylic acid
2-[N-(1-S-carbethoxy-3-phenylpropyl)-S-alanyl]-cis-octahydrocyclopenta[c]pyrrole-1-S-carboxylic acid
2-[N-(1-S-carbethoxy-3-cyclohexylpropyl)-S-alanyl]-cis-octahydrocyclopenta[c]pyrrole-1-S-carboxylic acid
2-[N-(1-S-carbethoxy-3-cyclohexylpropyl)-S-alanyl]-cis-octahydrocyclopenta[c]pyrrole-1-S-carboxylic acid benzyl ester
2-[N-(1-S-carbethoxy-3-cyclohexylpropyl)-S-lysyl]-cis-octahydrocyclopenta[c]pyrrole-1-S-carboxylic acid
1-[N-(1-S-carbethoxy-3-phenylpropyl)-S-alanyl]-2,3,3a,4,5,7a-hexahydroindole-cis-endo-2-S-carboxylic acid
1-[N-(1-S-carbethoxy-3-phenylpropyl)-S-lysyl]-2,3,3a,4,5,7a-hexahydroindole-cis-endo-2-S-carboxylic acid
2-[N-(1-S-carbethoxy-3-cyclohexylpropyl)-S-lysyl]-2-azabicyclo[3.1.0]hexane-3-S-carboxylic acid
2-[N-(1-S-carboxy-3-phenylpropyl)-S-lysyl]-2-azabicyclo[3.1.0]hexane-cis-endo-3-S-carboxylic acid
2-[N-(1-S-carbethoxy-3-cyclopentylpropyl)-S-alanyl]-2-azabicyclo[3.1.0]hexane-3-S-carboxylic acid
2-[N-(1-S-carbethoxy-3-phenylpropyl)-S-alanyl]-cis-endo-2-azabicyclo[3.1.0]hexane-3-S-carboxylic acid
2-[N-(1-S-carbethoxy-3-cyclohexylpropyl)-S-alanyl]-cis-endo-2-azabicyclo[3.1.0]hexane-3-S-carboxylic acid
1'-[N-(1-S-carbethoxy-3-phenylpropyl)-S-alanyl]-(3'S,5'S)-spiro-bicyclo[2.2.2]octane-2,3'-pyrrolidine-5'-carboxylic acid
1'-[N-(1-S-carbethoxy-3-phenylpropyl)-S-alanyl]-3'R,5'S)-spiro-bicyclo[2.2.2]octane-2,3'-pyrrolidine-5'-carboxylic acid
1'-[N-(1-S-carbethoxy-3-phenylpropyl)-S-alanyl]-(3'S,5'R)-spiro-bicyclo[2.2.2]octane-2,3'-pyrrolidine-5'-carboxylic acid
1'-[N-(1-S-carbethoxy-3-phenylpropyl)-S-alanyl]-(3'R,5'R)-spiro-bicyclo[2.2.2]octane-2,3'-pyrrolidine-5'-carboxylic acid
1'-[N-(1-R-carbethoxy-3-phenylpropyl)-S-alanyl]-(3'S,5'R)-spiro-bicyclo[2.2.2]octane-2,3'-pyrrolidine-5'-carboxylic acid
1'-[N-(1-R-carbethoxy-3-phenylpropyl)-S-alanyl]-(3'S,5'S)-spiro-bicyclo[2.2.2]octane,2,3'-pyrrolidine-5'-carboxylic acid
1'-[N-(1-R-carbethoxy-3-phenylpropyl)-S-alanyl]-(3'R,5'S)-spiro-bicyclo[2.2.2]octane-2,3'-pyrrolidine-5'-carboxylic acid
1'-[N-(1-R-carbethoxy-3-phenylpropyl)-S-alanyl]-(3'R,5'R)-spiro-bicyclo[2.2.2]octane-2,3'-pyrrolidine-5'-carboxylic acid
1'-[N-(1-S-carbethoxy-3-phenylpropyl)-R-alanyl]-(3'S,5'S)-spiro-bicyclo[2.2.2]octane-2,3'-pyrrolidine-5'-carboxylic acid
1'-[N-(1-S-carbethoxy-3-phenylpropyl)-R-alanyl]-(3'R,5'S)-spiro-bicyclo[2.2.2]octane-2,3'-pyrrolidine-5'-carboxylic acid
1'-[N-(1-S-carbethoxy-3-phenylpropyl)-R-alanyl]-(3'S,5'R)-spiro-bicyclo[2.2.2]octane-2,3'-pyrrolidine-5'-carboxylic acid
1'-[N-(1-S-carbethoxy-3-phenylpropyl)-R-alanyl]-(3'R,5'R)-spiro-bicyclo[2.2.2]octane-2,3'-pyrrolidine-5'-carboxylic acid
1'-[N-(1-R-carbethoxy-3-phenylpropyl)-R-alanyl]-(3'S,5'S)-spiro-bicyclo[2.2.2]octane-2,3'-pyrrolidine-5'-carboxylic acid
1'-[N-(1-R-carbethoxy-3-phenylpropyl)-R-alanyl]-(3'R,5'S)-spiro-bicyclo[2.2.2]octane-2,3'-pyrrolidine-5'-carboxylic acid 1'-[N-(1-R-carbethoxy-3-phenylpropyl)-R-alanyl]-(3'S,5'R)-spiro-bicyclo[2.2.2]octane-2,3'-pyrrolidine-5'-carboxylic acid 1'-[N-(1-R-carbethoxy-3-phenylpropyl)-R-alanyl]-(3'R,5'R)-spiro-bicyclo[2.2.2]octane-2,3'-pyrrolidine-5'-carboxylic acid These compounds can be prepared by, for example, the process described in German Patent Application P 33 33 455.2, in which the tert.-butyl or benzyl derivatives described in the application are converted in a known manner, by acid or alkaline hydrolysis or by hydrogenolysis catalyzed with noble metals, into the monocarboxylic acid derivatives. The $N^\epsilon$-benzyloxycarbonyl protective group of the lysine derivatives is removed by hydrogenolysis catalyzed with noble metals. The compounds listed above can readily be converted with physiologically tolerated acids or bases (in the case of mono- or dicarboxylic acids) into the corresponding salts (for example hydrochlorides, maleates, fumarates etc.), and be used as salts according to the invention.

The compounds of the formula I are inhibitors of angiotensin converting enzyme (ACE) or are intermediates in the preparation of such inhibitors, and they can also be used for controlling high blood pressure of a variety of etiologies. Some of the compounds of the formula I and processes for their preparation are disclosed in, for example, U.S. Pat. No. 4,129,571, U.S. Pat. No. 4,374,829, European Patent A-79522, European Patent A-79022, European Patent A-49658, European Patent A-51301, U.S. Pat. No. 4,454,292, U.S. Pat. No. 4,374,847, European Patent A-72352, U.S. Pat. No. 4,350,704, European Patent A-50800, European Patent A-46953, U.S. Pat. No. 4,344,949, European Patent A-84164, U.S. Pat. No. 4,470,972, European Patent A-65301 and European Patent A-52991. New compounds of the formula I are prepared in an analogous manner.

Orally effective ACE inhibitors (some of the active compounds already mentioned above) are also advantageous, such as, for example, ramipril, enalapril(f), captopril(a), lisinopril(g), cilazapril(o), RHC 3659, CGS 13945, CGS 13928C(l), CGS 14824A(h), CI-906(j), zofenopril(e), fosenopril(p), alacepril, CI-925(k), pentopril(q), CV 3317(m), indolapril(h), YS 980(b), fentiapril(c), pivopril(d), perindopril(i), and others. Orally effective ACE inhibitors are described in, for example, Brunner et al., J. Cardiovasc. Pharmacol. 7 (Suppl. I) [1985] 2-11.

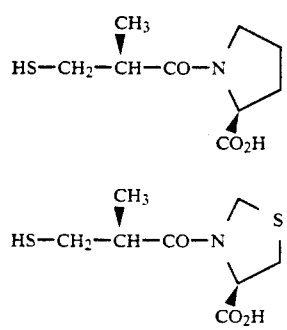
(a)

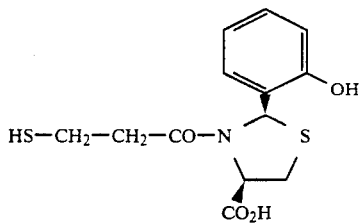
(b)

(c)
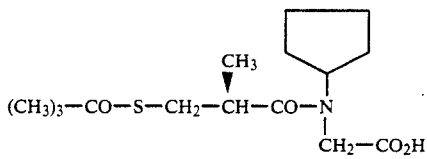

(d)
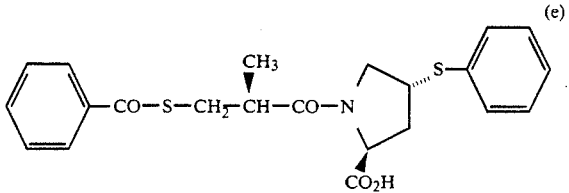

(e)
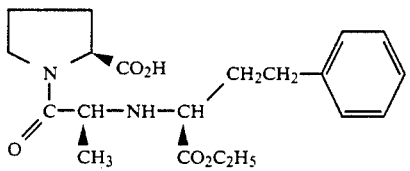

(f)
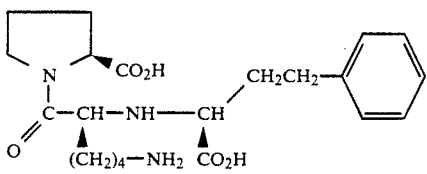

(g)
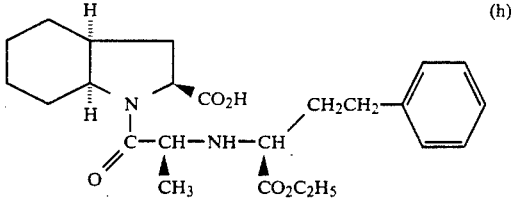

(h)
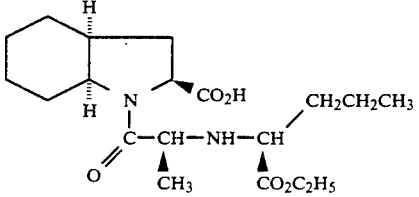

(i)

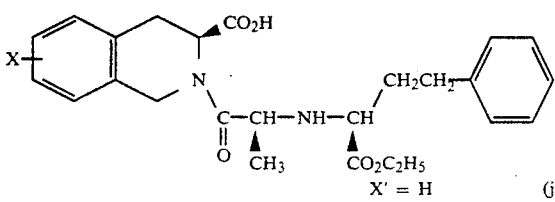

X' = H (j)
X' = 3,4 OCH₃ (k)

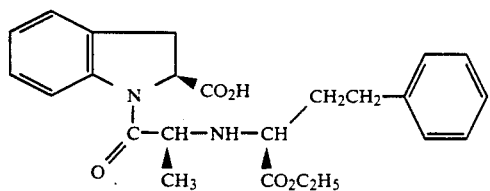

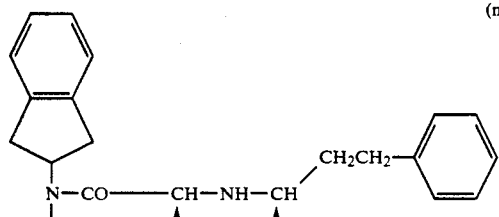

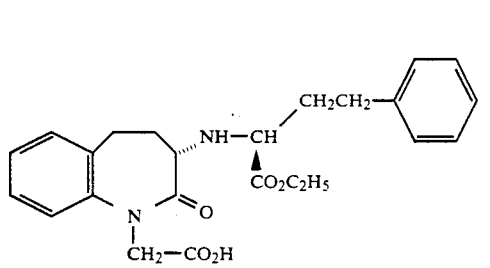

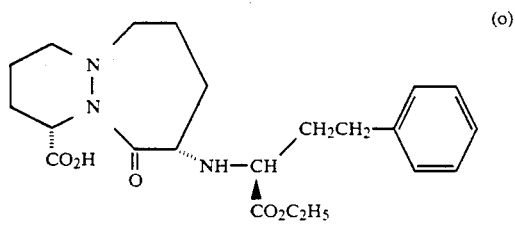

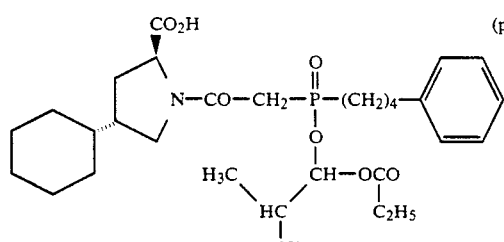

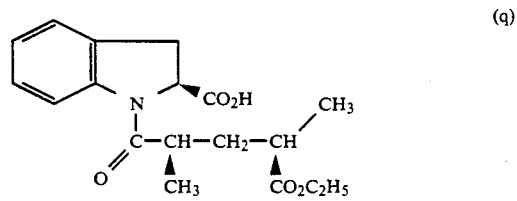

The ACE inhibitors which are disclosed in European Patent A-79022 and are of the formula III

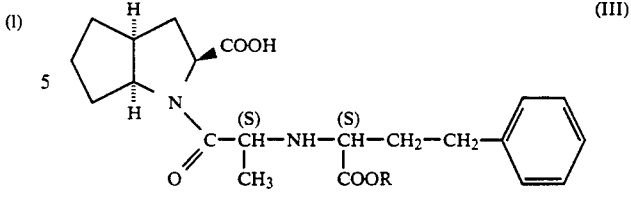

in which R denotes hydrogen, methyl, ethyl or benzyl, are preferred, in particular the compound of the formula III in which R denotes ethyl (ramipril).

Also preferred are the ACE inhibitors which are disclosed in European Patent A-84164 and are of the formula IV

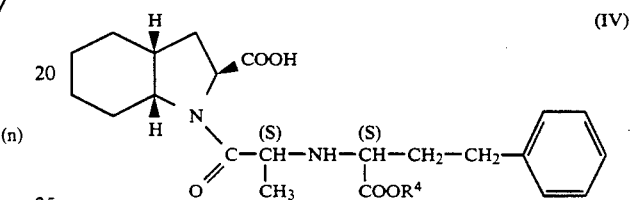

in which $R^4$ denotes hydrogen, $(C_1-C_4)$-alkyl or benzyl, in particular the compound of the formula IV in which $R^4$ denotes ethyl.

Furthermore, preference is given to 1'-[N-(1-S-carboethoxy-3-phenylpropyl)-S-alanyl]-exo- or endo-spirobicyclo[2.2.2]octane-2,3'-pyrrolidin-5'-ylcarboxylic acid and isomers, and (S,S,S)-1-methyl-2-(1-carbethoxy-3-phenylpropyl)-2H-undecahydrocyclopenta[4.5]pyrrolo[1,2-a]pyrazine-3,8-dione.

The invention also relates to new compounds of the formula II

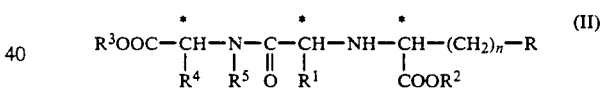

A. in which
I.
  a) n is 1 or 2;
  b) R
   1. denotes hydrogen;
   2. denotes alkyl having 1–18 carbon atoms;
   3. denotes an aliphatic acyclic radical of the formula $C_aH_{(2a-b+1)}$, in which double bonds, if their number exceeds 1, are not cumulative, a represents an integer 2 to 18, and b represents an integer 2 to a;
   4. denotes a mono-, di-, tri-, tetra- or pentacyclic, non-aromatic hydrocarbon radical of the formula $C_cH_{(2c-d-1)}$, which is optionally branched, in which c represents an integer 3 to 20, and d represents an even number 0 to (c−2);
   5. denotes aryl which has 6–12 carbon atoms and can be mono-, di- or trisubstituted by $(C_1-C_8)$-alkyl, $(C_1-C_4)$-alkoxy, hydroxyl, halogen, nitro, amino, aminomethyl, $(C_1-C_4)$-alkylamino, di-$(C_1-C_4)$alkylamino, $(C_1-C_4)$-alkanylamino, methylenedioxy, carboxyl, cyano and/or sulfamoyl;
   6. if n is 2, denotes $(C_6-C_{12})$-aryl-$(C_1-C_8)$-alkyl or di-$(C_6-C_{12})$-aryl-$(C_1-C_8)$-alkyl, each of which can be substituted in the aryl moiety as described under I.b)5; or
7. aryloxy having 1-4 carbon atoms;
8. alkoxy which has 6-12 carbon atoms and can be substituted as described under I.b)5;
9. mono- or bicyclic heteroaryloxy or heteroaryl $(C_1-C_8)$-alkyl which has 5-7 or 8-10 ring atoms respectively, up to 9 of these ring atoms representing carbon and 1 to 2 ring atoms representing sulfur or oxygen and/or 1 to 4 ring atoms representing nitrogen, and which can be substituted in the heteroaryl as described under I.b)5;
10. amino-$(C_1-C_8)$-alkyl;
11. $(C_1-C_4)$-alkanoylamino-$(C_1-C_8)$-alkyl;
12. $(C_7-C_{13})$-aroylamino-$(C_1-C_8)$-alkyl;
13. $(C_1-C_4)$-alkoxycarbonylamino-$(C_1-C_8)$-alkyl;
14. $(C_6-C_{12})$-aryl-$(C_1-C_4)$-alkoxycarbonylamino-$(C_1-C_8)$-alkyl;
15. $(C_6-C_{12})$-aryl-$(C_1-C_4)$-alkylamino-$(C_1-C_8)$-alkyl;
16. $(C_1-C_4)$-alkylamino-$(C_1-C_8)$-alkyl;
17. di-$(C_1-C_4)$-alkylamino-$(C_1-C_8)$-alkyl;
18. guanidino-$(C_1-C_8)$-alkyl,
19. imidazolyl;
20. indolyl;
21. $(C_1-C_4)$-alkylthio;
22. if n is 2, $(C_1-C_4)$-alkylthio-$(C_1-C_8)$-alkyl;
23. $(C_6-C_{12})$-arylthio-$(C_1-C_8)$-alkyl which can be substituted in the aryl moiety as described under I.b)5;
24. $(C_6-C_{12})$-aryl-$(C_1-C_8)$-alkylthio which can be substituted in the aryl moiety as described under I.b)5;
25. if n is 2, carboxy-$(C_1-C_8)$-alkyl;
26. carboxyl;
27. carbamoyl;
28. if n is 2, carbamoyl-$(C_1-C_8)$-alkyl;
29. $(C_1-C_4)$-alkoxycarbonyl-$(C_1-C_8)$-alkyl;
30. if n is 2, $(C_6-C_{12})$-aryloxy-$(C_1-C_8)$-alkyl which can be substituted in the aryl moiety as described under I.b)5; or
31. denotes $(C_6-C_{12})$-aryl-$(C_1-C_8)$-alkoxy which can be substituted in the aryl moiety as described under I.b)5;
c) $R^1$
1. denotes hydrogen;
2. denotes alkyl having 1-18 carbon atoms;
3. denotes an acyclic aliphatic radical of the formula $C_aH_{(2a-b+1)}$, in which double bonds, if their number exceeds 1, are not cumulative, a represents an integer 2 to 18, and b represents an even number 2 to a;
4. denotes a mono-, di-, tri-, tetra- or pentacyclic, non-aromatic hydrocarbon radical of the formula $C_cH_{(2c-d-1)}$, which is optionally branched, in which c represents an integer 3 to 20, and d represents an even number 0 to $(c-2)$;
5. aryl which has 6-12 carbon atoms and can be substituted as described under I.b)5;
6. $(C_6-C_{12})$-aryl-$(C_1-C_8)$-alkyl or $(C_7-C_{13})$-aroyl-$(C_1-C_8)$-alkyl, both of which can be substituted as for aryl under I.b)5;
7. mono- or bicyclic, optionally partially hydrogenated, heteroaryl or heteroaryl-$(C_1-C_8)$-alkyl which has 5-7 or 8-10 ring atoms respectively, up to 9 of these ring atoms representing carbon and 1 or 2 ring atoms representing sulfur or oxygen and/or 1 to 4 ring atoms representing nitrogen, and which can be substituted in the heteroaryl as described for aryl under I.b)5; or
8. if not already covered by c) 1.-8., the optionally protected side-chain of a naturally occurring α-amino acid of the formula $R^1$—CH(NH$_2$)—COOH;
d) $R^2$ and $R^3$ are identical or different and
1. denote hydrogen;
2. alkyl having 1-18 carbon atoms;
3. denote an aliphatic acyclic radical of the formula $C_aH_{(2a-b+1)}$, in which double bonds, if their number exceeds 1, are not cumulative, a represents an integer 2 to 18, and b represents an even number 2 to a;
4. a mono-, di-, tri-, tetra- or pentacyclic, non-aromatic hydrocarbon radical of the formula $C_cH_{(2c-d-1)}$, which is optionally branched and in which c represents an integer 3 to 20, and d represents an even number 0 to $(c-2)$;
5. di-$(C_1-C_4)$-alkylamino-$(C_1-C_8)$-alkyl;
6. $(C_1-C_5)$-alkanoyloxy-$(C_1-C_8)$-alkyl;
7. $(C_1-C_6)$-alkoxycarbonyloxy-$(C_1-C_8)$-alkyl;
8. $(C_7-C_{13})$-aroyloxy-$(C_1-C_8)$-alkyl;
9. $(C_6-C_{12})$-aryloxycarbonyloxy-$(C_1-C_8)$-alkyl;
10. aryl having 6-12 carbon atoms; or
11. denote $(C_7-C_{20})$-aralkyl; it being possible for the radicals mentioned under d) 8., 9., 10. and 11. to be substituted in the aryl moiety as described under I.b)5; and
e) $R^4$ and $R^5$ form, together with the atoms carrying them, a mono-, bi- or tricyclic heterocyclic ring system having 3 to 15 ring carbon atoms,
and physiologically acceptable salts thereof.
II. excepting compounds of the formula II and their salts in which
a) n is 1 or 2,
b) R denotes
1. hydrogen,
2. alkyl having 1-8 carbon atoms,
3. alkenyl having 2-6 carbon atoms,
4. cycloalkyl having 3-9 carbon atoms,
5. aryl which has 6-12 carbon atoms and can be mono-, di- or trisubstituted by $(C_1-C_4)$-alkyl, $(C_1-C_4)$-alkoxy, hydroxy, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl,
6. alkoxy having 1-4 carbon atoms,
7. aryloxy which has 6-12 carbon atoms and can be substituted as described under II. b) 5;
8. mono- or bicyclic heteroaryloxy which has 5-7 or 8-10 ring atoms respectively, 1 to 2 of these ring atoms representing sulfur or oxygen atoms, and/or 1 to 4 of these ring atoms representing nitrogen, and which can be substituted as described under II.b)5.;
9. amino-$(C_1-C_4)$-alkyl,
10. $(C_1-C_4)$-alkanoylamino-$(C_1-C_4)$alkyl,
11. $(C_7-C_{13})$-aroylamino-$(C_1-C_4)$-alkyl, 12. (C₁-C₄)-alkoxycarbonylamino-(C₁-C₄)-alkyl,
13. (C₆-C₁₂)-aryl-(C₁-C₄)-alkoxycarbonylamino-(C₁-C₄)-alkyl,
14. (C₆-C₁₂)-aryl-(C₁-C₄)-alkylamino-(C₁-C₄)-alkyl,
15. (C₁-C₄)-alkylamino-(C₁-C₄)-alkyl,
16. di-(C₁-C₄)-alkylamino-(C₁-C₄)-alkyl,
17. guanidino-(C₁-C₄)-alkyl,
18. imidazolyl,
19. indolyl;
20. (C₁-C₄)-alkylthio,
21. (C₁-C₄)-alkylthio-(C₁-C₄)-alkyl,
22. (C₆-C₁₂)-arylthio-(C₁-C₄)-alkyl which can be substituted in the aryl moiety as described under II.b)5;
23. (C₆-C₁₂)-aryl-(C₁-C₄)-alkylthio which can be substituted in the aryl moiety as described under II.b)5;
24. carboxy-(C₁-C₄)-alkyl,
25. carboxyl,
26. carbamoyl,
27. carbamoyl-(C₁-C₄)-alkyl,
28. (C₁-C₄)-alkoxycarbonyl-(C₁-C₄)-alkyl,
29. (C₆-C₁₂)-aryloxy-(C₁-C₄)-alkyl which can be substituted in the aryl moiety as described under II.b)5; or (C₆-C₁₂)-aryl-(C₁-C₄)-alkoxy which can be substituted in the aryl moiety as described under II.b)5;

c) R¹ denotes
1. hydrogen,
2. alkyl having 1-6 carbon atoms,
3. alkenyl having 2-6 carbon atoms,
4. alkynyl having 2-6 carbon atoms,
5. cycloalkyl having 3-9 carbon atoms,
6. cycloalkenyl having 5-9 carbon atoms,
7. (C₃-C₉)-cycloalkyl-(C₁-C₄)-alkyl,
8. (C₅-C₉)-cycloalkenyl-(C₁-C₄)-alkyl,
9. optionally partially hydrogenated aryl which has 6-12 carbon atoms and can be substituted as described under II.b)5;
10. (C₆-C₁₂)-aryl-(C₁-C₄)-alkyl or (C₇-C₁₃)-aroyl-(C₁ or C₂)-alkyl, both of which can be substituted in the aryl moiety as described under II.b)5;
11. mono- or bicyclic, optionally partially hydrogenated heteroaryl which has 5-7 or 8-10 ring atoms respectively, 1 to 2 of these ring atoms representing sulfur or oxygen atoms, and/or 1 to 4 of these ring atoms representing nitrogen atoms, and which can be substituted as described under II.b)5; or
12. if not embraced by the above definitions, the optionally protected side-chain of a naturally occurring α-amino acid of the formula R¹—CH(NH₂)—COOH;

d) R² and R³ are identical or different and denote
1. hydrogen,
2. alkyl having 1-6 carbon atoms,
3. alkenyl having 2-6 carbon atoms,
4. di-(C₁-C₄)-alkylamino-(C₁-C₄)-alkyl,
5. (C₁-C₅)-alkanoyloxy-(C₁-C₄)-alkyl,
6. (C₁-C₆)-alkoxycarbonyloxy-(C₁-C₄)-alkyl,
7. (C₇-C₁₃)-aroyloxy-(C₁-C₄)-alkyl,
8. (C₆-C₁₂)-aryloxycarbonyloxy-(C₁-C₄)-alkyl,
9. aryl having 6-12 carbon atoms,
10. (C₆-C₁₂)-aryl-(C₁-C₄)-alkyl,
11. (C₃-C₉)-cycloalkyl or
12. (C₃-C₉)-cycloalkyl-(C₁-C₄)-alkyl, and e) R⁴ and R⁵ have the meaning defined under I.e), B. and compounds of the formula II in which
a) n is 1 or 2;
b) R denotes
1. hydrogen;
2. alkyl having 1-8 carbon atoms;
3. alkenyl having 2-6 carbon atoms;
4. cycloalkyl having 3-9 carbon atoms;
5. aryl which has 6-12 carbon atoms and can be mono-, di- or trisubstituted by (C₁-C₄)-alkyl, (C₁-C₄)-alkoxy, hydroxyl, halogen, nitro, amino, aminomethyl, (C₁-C₄)-alkylamino, di-(C₁-C₄)-alkylamino, (C₁-C₄)-alkanoylamino, methylenedioxy, carboxyl, cyano and/or sulfamoyl;
6. alkoxy having 1-4 carbon atoms;
7. aryloxy which has 6-12 carbon atoms and can be substituted as described under B.b)5;
8. mono- or bicyclic heteroaryloxy which has 5-7 or 8-10 ring atoms respectively, up to 9 of these ring atoms representing carbon and 1 or 2 of these ring atoms representing sulfur or oxygen and/or 1 to 4 of these ring atoms representing nitrogen, and which can be substituted as described under B.b)5;
9. amino-(C₁-C₄)-alkyl;
10. (C₁-C₄)-alkanoylamino-(C₁-C₄)-alkyl;
11. (C₇-C₁₃)-aroylamino-(C₁-C₄)-alkyl;
12. (C₁-C₄)-alkoxycarbonylamino-(C₁-C₄)-alkyl;
13. (C₆-C₁₂)-aryl-(C₁-C₄)-alkoxycarbonylamino-(C₁-C₄)-alkyl;
14. (C₆-C₁₂)-aryl-(C₁-C₄)-alkylamino-(C₁-C₄)-alkyl;
15. (C₁-C₄)-alkylamino-(C₁-C₄)-alkyl;
16. di-(C₁-C₄)-alkylamino-(C₁-C₄)-alkyl;
17. guanidino-(C₁-C₄)-alkyl;
18. imidazolyl;
19. indolyl;
20. (C₁-C₄)-alkylthio;
21. if n is 2, (C₁-C₄)-alkylthio-(C₁-C₄)-alkyl;
22. (C₆-C₁₂)-arylthio-(C₁-C₄)-alkyl which can be substituted in the aryl moiety as described under B.b)5;
23. (C₆-C₁₂)-aryl-(C₁-C₄)-alkylthio which can be substituted in the aryl moiety as described under B.b)5;
24. if n is 2, carboxy-(C₁-C₄)-alkyl;
25. carboxyl;
26. carbamoyl;
27. if n is 2, carbamoyl-(C₁-C₄)-alkyl;
28. (C₁-C₄)-alkoxycarbonyl-(C₁-C₄)-alkyl;
29. if n is 2, (C₆-C₁₂)-aryloxy-(C₁-C₄)-alkyl which can be substituted in the aryl moiety as described under B.b)5; or
30. (C₆-C₁₂)-aryl-(C₁-C₄)-alkoxy which can be substituted in the aryl moiety as described under B.b)5;

c) R¹ represents the side-chain of valine, leucine, norvaline, norleucine, methionine, ornithine, cyclohexylalanine, 2-thienylalanine, 3-thienylalanine, O-(C₃-C₅)-alkyltyrosine, isoleucine, isovaline or C-phenylglycine;

d) R² and R³ are identical or different and denote
1. hydrogen;

2. alkyl having 1-6 carbon atoms;
3. alkenyl having 2-6 carbon atoms;
4. di-$(C_1-C_4)$-alkylamino-$(C_1-C_4)$-alkyl;
5. $(C_1-C_5)$-alkanoyloxy-$(C_1-C_4)$-alkyl;
6. $(C_1-C_6)$-alkoxycarbonyloxy-$(C_1-C_4)$-alkyl;
7. $(C_7-C_{13})$-aroyloxy-$(C_1-C_4)$-alkyl;
8. $(C_6-C_{12})$-aryloxycarbonyloxy-$(C_1-C_4)$-alkyl;
9. aryl having 6-12 carbon atoms;
10. $(C_6-C_{12})$-aryl-$(C_1-C_4)$-alkyl;
11. $(C_3-C_9)$-cycloalkyl; or
12. $(C_3-C_9)$-cycloalkyl-$(C_1-C_4)$-alkyl, and e) $R^4$ and $R^5$ have the meaning defined under A.I.e), and their physiologically tolerated salts, or C. in which
  a) n, R, $R^4$ and $R^5$ are as defined above under B. and
  b) $R^1$ represents the side-chain of alanine, lysine or ε-acyllysine, and
  c) $R^2$ and $R^3$ are identical or different and denote propyl, isopropyl, n-butyl, isobutyl, sec.-butyl, n-pentyl, sec.-pentyl, iso-pentyl, neopentyl, n-hexyl, isohexyl, cyclobutyl, cyclopentyl, cyclohexyl, cycloheptyl, cyclooctyl, cyclohexenyl, cycloheptenyl, phenyl, α- or β-naphthyl, 2-, 3- or 4-biphenylyl, phenethyl, 3-phenylpropyl, benzhydryl, α-methylbenzyl, α-methylenebenzyl, 2-, 3- or 4-phenylbenzyl, bibenzyl-α-yl, styryl, 1-indanyl or 9-fluorenyl, with phenyl, and phenyl as a part-structure of one of the said radicals, being substituted as defined, where appropriate, under A.II.b)5,
  or one of the radicals $R^2$ and $R^3$ denotes hydrogen, and the other is as defined above,
  or $R^2$ represents benzyl, and $R^3$ represents benzyl, hydrogen or one of the abovementioned definitions, and their physiologically tolerated salts.

$R^4$ and $R^5$ form, together with the atoms carrying them, preferably a mono-, bi- or tricyclic heterocyclic ring system which has 3 to 15 ring carbon atoms and up to 2, preferably up to 1, ring sulfur atom(s) and up to 1, preferably no, additional ring nitrogen atom, preferably from the series comprising pyrrolidine, thiazolidine, tetrahydroisoquinoline, decahydroisoquinoline, octahydroindole, indoline, octahydrocyclopenta[b]pyrrole, 2-azaspiro[4.5]decane, 2-azaspiro[4.4]nonane, spiro[(bicyclo[2.2.1]heptane)-2,3'-pyrrolidine], spiro[(bicyclo[2.2.2]octane-2,3'-pyrrolidine], 2-azatricyclo[4.3.0.1$^{6,9}$]decane, decahydrocyclohepta[b]pyrrole, octahydroisoindole, octahydrocyclopenta[c]pyrrole, 2,3,3a,4,5,7a-hexahydroindole, 1,2,3,3a,4,5a-hexahydrocyclopenta[b]pyrrole and 2-azabicyclo[3.1.0]hexane.

Suitable salts of the compounds of the formulae I and II are, depending on the acidic or basic nature of these compounds, alkali metal or alkaline earth metal salts or salts with physiologically tolerated amines, or salts with inorganic or organic acids such as, for example, HCl, HBr, $H_2SO_4$, maleic acid, fumaric acid, tartaric acid and citric acid.

The capillary structure of the blood vessels in the brain differs from that in other regions of the body. The brain capillaries are surrounded by a layer of endothelial cells which are particularly closely linked together (by tight junctions). In addition, brain capillaries have very many fewer of the pores through which, in other blood capillaries, low molecular weight substances can penetrate into or emerge from the surrounding tissue. In this way, in the brain capillaries the property of lipid solubility has a very much greater importance for partition between blood and surrounding tissue than is the case for the remainder of the body.

Hence the preferred compounds of the formula II are those in which at least one of the radicals R, $R^1$, $R^2$ and $R^3$ represents a lipophilic radical, such as a long-chain aliphatic, alicyclic-aliphatic, araliphatic or heteroaraliphatic radical, a sufficiently large alicyclic radical, or an appropriately substituted alicyclic, aromatic or heteroaromatic radical, or contains a radical of this type as a part-structure.

In this respect, particularly suitable compounds of the formula II are those in which
  R denotes
  1. $(C_9-C_{18})$-alkyl;
  2. $(C_7-C_{18})$-alkenyl;
  3. a radical which has 4–18 carbon atoms and is defined as above under A.I.b)3 and in which b≧4;
  4. a radical which has 4–20 carbon atoms and is defined as above under A.1.b)4 and in which d≧2;
  5 is as defined above under A.I.b)5;
  6. heteroarylalkyl which is defined as above under A.I.b)9;
  7. amino-$(C_5-C_8)$-alkyl;
  8. amino-$(C_5-C_8)$-alkyl;
  9. $(C_1-C_4)$-alkanoylamino-$(C_5-C_8)$-alkyl;
  10. $(C_7-C_{13})$-aroylamino-$(C_5-C_8)$-alkyl;
  11. $(C_1-C_4)$-alkoxycarbonylamino-$(C_5-C_8)$-alkyl;
  12. $(C_6-C_{12})$-aryl-$(C_1-C_4)$-alkoxycarbonylamino-$(C_5-C_8)$-alkyl;
  13. $(C_6-C_{12})$-aryl-$(C_1-C_4)$-alkylamino-$(C_5-C_8)$-alkyl;
  14. $(C_1-C_4)$-alkylamino-$(C_5-C_8)$-alkyl;
  15. di-$(C_1-C_4)$-alkylamino-$(C_5-C_8)$-alkyl;
  16. guanidino-$(C_5-C_8)$-alkyl;
  17. if n is 2, $(C_1-C_4)$-alkylthio-$(C_5-C_8)$-alkyl;
  18. $(C_6-C_{12})$-arylthio-$(C_5-C_8)$-alkyl which can be substituted in the aryl moiety as described above under A.I.b)5;
  19. $(C_6-C_{12})$-aryl-$(C_5-C_8)$-alkylthio which can be substituted in the aryl moiety as described above under A.I.b)5;
  20. if n is 2, carboxy-$(C_5-C_8)$-alkyl;
  21. carbamoyl-$(C_5-C_8)$-alkyl;
  22. $(C_1-C_4)$-alkoxycarbonyl-$(C_5-C_4)$-alkyl;
  23. if n is 2, $(C_6-C_{12})$-aryloxy-$(C_5-C_8)$-alkyl which can be substituted in the aryl moiety as described above under A.I.b)5; or
  24. $(C_6-C_{12})$-aryl-$(C_5-C_8)$-alkoxy which can be substituted in the aryl moiety as described above under A.I.b)5.

Additional compounds of the formula II which are suitable are those in which
  $R^1$ denotes
  1. $(C_7-C_{18})$-alkyl;
  2. $(C_7-C_{18})$-alkenyl;
  3. $(C_7-C_{18})$-alkynyl;

4. a radical which has 4–18 carbon atoms and is defined as above under A.I.c)3. and in which b≧2 and only double bonds are present;
5. a radical which is as defined above under A.I.c)4, excepting cycloalkyl and cycloalkenyl having up to 9 carbon atoms;
6. optionally substituted $(C_6-C_{12})$-aryl-$(C_5-C_8)$-alkyl;
7. optionally substituted $(C_7-C_{13})$-aroyl-$(C_3-C_8)$-alkyl or
8. optionally substituted heteroaryl-$(C_1-C_8)$-alkyl, and those compounds of the formula II in which $R^1$ represents the side-chain of valine, leucine, norvaline, norleucine, methionine, ornithine, cyclohexylalanine, 2-thienylalanine, 3-thienylalanine, O-$(C_3-C_5)$-alkyltyrosine, isoleucine, isovaline or C-phenylglycine.

$R^2$ and $R^3$ are then identical or different and preferably denote
1. $(C_7-C_{18})$-alkyl;
2. $(C_7-C_{18})$-alkenyl;
3. a radical which has 4–18 carbon atoms and is defined as above under A.I.d)3. and in which b>4;
4. a radical which is as defined above under A.I.d)4, excepting $(C_3-C_9)$-cycloalkyl and $(C_3-C_9)$-cycloalkyl-$(C_1-C_4)$-alkyl;
5. di-$(C_1-C_4)$-alkylamino-$(C_5-C_8)$-alkyl;
6. $(C_1-C_5)$-alkanoyloxy-$(C_5-C_8)$-alkyl;
7. $(C_1-C_6)$-alkoxycarbonyloxy-$(C_5-C_8)$-alkyl;
8. $(C_7-C_{13})$-aroyloxy-$(C_5-C_8)$-alkyl;
9. $(C_6-C_{12})$-aryloxycarbonyloxy-$(C_5-C_8)$-alkyl;
10. $(C_{16}-C_{20})$-aralkyl;
it being possible for the radicals mentioned under d)8., 9. and 10. to be substituted in the aryl moiety as described above under A.I.b)5.; or one of the radicals $R^2$ and $R^3$ denotes hydrogen and the other is as defined above.

In addition, preferred compounds of the formula II are those in which $R^2$ and $R^3$ are identical or different and denote propyl, isopropyl, n-butyl, isobutyl, sec.-butyl, n-pentyl, sec.-pentyl, isopentyl, neopentyl, n-hexyl, isohexyl, cyclobutyl, cyclopentyl, cyclohexyl, cycloheptyl, cyclooctyl, cyclohexenyl, cycloheptenyl, menthyl, phenyl, α- or β-naphthyl, 2-, 3- or 4-biphenylyl, phenethyl, 3-phenylpropyl, benzhydryl, α-methylbenzyl, α-methylenebenzyl, 2-, 3- or 4-phenylbenzyl, bibenzyl-α-yl, styryl, 1-indanyl or 9-fluorenyl, with phenyl, and phenyl as a part-structure of one of the said radicals, optionally being substituted as defined above under A.I.b)5., or one of the radicals $R^2$ and $R^3$ denotes hydrogen and the other is as defined above, or $R^2$ represents benzyl, and $R^3$ represents benzyl, hydrogen or one of the abovementioned definitions.

The invention also relates to a process for the preparation of a compound of the formula II, which comprises reacting together its fragments in a suitable solvent, where appropriate in the presence of a base and/or of a coupling aid, reducing, where appropriate, unsaturated compounds which have formed as intermediates, such as Schiff's bases, eliminating protective groups which have been introduced temporarily to protect reactive groups, esterifying, where appropriate, compounds of the formula II having one or more free carboxyl groups, and converting, where appropriate, the resulting compounds into their physiologically tolerated salts.

It is possible, for example, in the said manner to react compounds of the formula V with compounds of the formula VI.

(V)

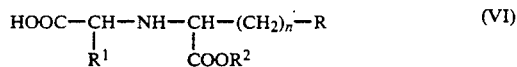
(VI)

The reaction of these compounds can be carried out, for example, in analogy to known peptide coupling methods in an organic solvent such as DMF, $CH_2Cl_2$ or DMA in the presence of coupling aids such as carbodiimides (for example dicyclohexylcarbodiimide), diphenylphosphoryl azide, alkanephosphoric anhydrides, dialkylphosphinic anhydrides or N,N-succinimidyl carbonate, in a solvent such as $CH_3CN$. Amino groups in compounds of the formula V can be activated with tetraethyl diphosphite. The compounds of the formula VI can be converted into active esters (for example with 1-hydroxybenzotriazole), mixed anhydrides (for example with chloroformic esters), azides or carbodiimide derivatives and thus activated (cf. Schröder, Lübke, The Peptides, volume 1, New York 1965, pages 76–136). The reaction is preferably carried out between −20° C. and the boiling point of the reaction mixture.

It is likewise possible to react compounds of the formula VII with compounds of the formula VIII with the formation of compounds of the formula II

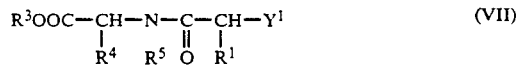
(VII)

(VIII)

in which either $Y^1$ represents amino and $Y^2$ represents a leaving group, or $Y^1$ represents a leaving group and $Y^2$ represents amino. Examples of suitable leaving groups are Cl, Br, I, alkylsulfonyloxy or arylsulfonyloxy.

Alkylations of this type are expediently carried out in water or an organic solvent such as a lower aliphatic alcohol (such as ethanol), benzyl alcohol, acetonitrile, nitromethane or glycol ethers, at a temperature between −20° C. and the boiling point of the reaction mixture, in the presence of a base such as an alkali metal hydroxide or an organic amine.

Furthermore, it is possible to condense compounds of the formula IX with compounds of the formula X

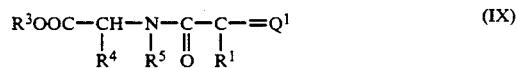
(IX)

(X)

in which either $Q^1$ represents amino+hydrogen and $Q^2$ represents oxo, or $Q^1$ represents oxo and $Q^2$ represents amino+hydrogen. The condensation is expediently carried out in water or an organic solvent such as a lower aliphatic alcohol, at a temperature between −20° C. and the boiling point of the reaction mixture, in the presence of a reducing agent, such as $NaBH_3CN$, compounds of the formula I being obtained directly. However, it is also possible to reduce Schiff's bases or enamines which are produced as intermediates, where appropriate after previous isolation, with the formation of compounds of the formula II, for example by hydrogenation in the presence of a transition metal catalyst.

Finally, reaction of compounds of the formula IX ($Q^1 = H + NH_2$) with compounds of the formula XI, or their reaction with compounds of the formula XII and XIII, expediently in the presence of a base such as sodium alcoholate, in an organic solvent such as a lower alcohol, at a temperature between $-10°$ C. and the boiling point of the reaction mixture, also results in compounds of the formula II ($n = 2$), $$R^2OOC\text{---}CH\text{=}CH\text{---}COR \quad \text{(XI)}$$

$$OCH\text{---}COOR^2 \quad \text{(XII)}$$

$$R\text{---}CO\text{---}CH_3 \quad \text{(XIII)}$$

with Schiff's bases which have been produced as intermediates being reduced as described above, and a carbonyl group being converted by reduction (for example with a complex hydride) into methylene.

In the abovementioned formulae V–XIII, $R$–$R^5$ and $n$ are as defined in formula II. Protective groups temporarily introduced to protect reactive groups not involved in the reaction are eliminated in a manner known per se after the reaction is complete (cf. Schröder, Lübke, loc. cit., pages 1–75 and 246–270; Greene, "Protective Groups in Organic Synthesis", New York 1981).

The new compounds of the general formula I or II can also be prepared, for example, using methods of esterification familiar to the expert (see, for example, Buchler, Pearson, Survey of Organic Syntheses, vol. 1, New York 1970, pages 802–825; Houben-Weyl, Methoden der Organischen Chemie, (Methods of Organic Chemistry), volume E5, 1985, pages 656–773).

a) Reaction of a mono- or dicarboxylic acid of the general formula I or II in which at least one of the radicals $R^2$ and $R^3$ denotes hydrogen with an appropriate alcohol with acid catalysis (mineral acid or acid ion exchanger).

b) Alkylation of a mono- or dicarboxylic acid of the general formula I or II in which at least one of the radicals $R^2$ and $R^3$ denotes hydrogen with a compound $R^2Z$ or $R^3Z$, in which Z denotes a leaving group which can be displaced nucleophilically (such as halogen, tosylate), in a polar protic or dipolar aprotic solvent, in the presence of a base such as an alkali metal hydroxide or alcoholate.

c) Reaction of a mono- or dicarboxylic acid of the general formula I or II in which at least one of the radicals $R^2$ and $R^3$ denotes hydrogen with a diazoalkene in an inert organic solvent such as $CH_2Cl_2$.

The cognition adjuvant action of the compounds according to the invention has been tested in the inhibitory (passive) avoidance test (step-through model) in mice having a body weight of 20–25 g. A modified form of the test method described by J. KOPP, Z. BODANECKY and M. E. JARVIK has been described by J. BURES, O. BURESOVA and J. HUSTON in "Techniques and Basic Experiments for the Study of Brain and Behavior", Elsevier Scientific Publishers, Amsterdam (1983).

According to the statements in this literature, a substance is said to have cognition adjuvant activity when it is able to abolish the amnesia induced in the experimental animals by an electroconvulsive shock or the amnesia induced by scopolamine.

The experiments were carried out by modified test methods. The comparison compound used was the known cognition adjuvant 2-oxo-1-pyrrolidinylacetamide (piracetam). The marked superiority of the compounds according to the invention over the comparison substance was evident from the fact that the scopolamine-induced amnesia in the inhibitory avoidance test can be abolished with an oral MED (minimal effective dose) of 1.0–30 mg/kg. The comparison substance has an oral MED of about 500–1,000 mg/kg.

Most of the compounds according to the invention have only low toxicity.

By reason of their pharmacological properties, the compounds according to the invention are suitable not only for the treatment of high blood pressure but also for the treatment of cognitive dysfunctions of various etiologies, as occur with, for example, Alzheimer's disease or senile dementia.

Hence the invention also relates to the use of the compounds according to the invention for the treatment and prophylaxis of cognitive dysfunctions in patients with high blood pressure.

The invention furthermore embraces medicaments containing the said compounds, processes for their preparation and the use of the compounds according to the invention for the preparation of medicaments which can be used for the treatment and prophylaxis of the abovementioned diseases.

It is possible, in practicing the method according to the invention, to use the angiotensin converting enzyme inhibitors which are described above in mammals such as monkeys, dogs, cats, rats, humans etc.

The medicaments are prepared by processes which are known per se and familiar to those skilled in the art. The pharmacologically active compounds (= active compound) according to the invention are used as medicaments either as such or, preferably, combined with suitable pharmaceutical auxiliaries, in the form of tablets, coated tablets, capsules, suppositories, emulsions, suspensions or solutions, the content of active compound being up to about 95%, preferably between 10 and 75%.

The auxiliaries suitable for the desired medicament formulation are familiar to those skilled in the art by reason of their expert knowledge. Apart from solvents, gel-forming agents, suppository bases, tabletting auxiliaries and other active compound vehicles, it is possible to use, for example, antioxidants, dispersing agents, emulsifiers, antifoam agents, masking flavors, preservatives, solubilizers or colorants.

The active compounds can, for example, be administered orally, rectally or parenterally (for example intravenously or subcutaneously), oral administration being preferred.

For a form for oral use, the active compounds are mixed with the additives suitable for this purpose, such as excipients, stabilizers or inert diluents, and converted by the customary methods into suitable presentations such as tablets, coated tablets, hard gelatin capsules, aqueous, alcoholic or oily suspensions, or aqueous, alcoholic or oily solutions. Examples of inert vehicles which can be used are gum arabic, magnesia, magnesium carbonate, lactose, glucose or starch, in particular corn starch. This formulation can take the form of dry and of moist granules. Examples of suitable oily excipients or solvents are vegetable or animal oils such as sunflower oil or fishliver oil.

For subcutaneous or intravenous administration, the active compounds or their physiologically tolerated salts are converted into solutions, suspensions or emulsions, if appropriate with the substances customary for this purpose such as solubilizers, emulsifiers or other auxiliaries. Examples of suitable solvents are water, physiological saline solution or alcohols such as ethanol, propanol, glycerol, and in addition also sugar solutions such as glucose or mannitol solutions, as well as a mixture of the various solvents mentioned.

The following examples 1-6 indicate the forms used for the prophylaxis and treatment of cognitive dysfunctions by the method according to the invention. The compounds according to the invention can be converted into the appropriate use forms in analogy to the examples.

EXAMPLE 1

Preparation of the agent used according to the invention for oral use in the treatment and prophylaxis of cognitive dysfunctions.

1000 tablets each containing 10 mg of 2-[N-(1-S-carbethoxy-3-phenylpropyl)-S-alanyl]-1S,3S,5S-2-azabicyclo[3.3.0]-octane-3-carboxylic acid are prepared using the following auxiliaries:

| | |
|---|---|
| 2-[N-(1-S-carbethoxy-3-phenylpropyl)-S-alanyl]-(1S,3S,5S)-2-azabicyclo[3.3.0]octane-3-carboxylic acid | 10 g |
| corn starch | 140 g |
| gelatin | 7.5 g |
| microcrystalline cellulose | 2.5 g |
| magnesium stearate | 2.5 g |

2-[N-(1-S-Carbethoxy-3-phenylpropyl)-S-alanyl]-(1S,3S,5S)-2-azabicyclo[3.3.0]octane-3-carboxylic acid and corn starch are mixed with an aqueous gelatin solution. The mixture is dried and milled to form granules. Microcrystalline cellulose and magnesium stearate are mixed with the granules.

The resulting granules are compressed to form 1000 tablets, each tablet containing 10 mg of the ACE inhibitor. These tablets can be used for the treatment and prophylaxis of cognitive dysfunctions.

EXAMPLE 2

In analogy to Example 1, 1000 tablets each containing 10 mg of 1'-[N-(1-S-carbethoxy-3-phenylpropyl)-S-alanyl]-(3'S,5'S)-spirobicyclo[2.2.2]octane-2,3'-pyrrolidine-5'-carboxylic acid are prepared.

EXAMPLE 3

Gelatin capsules each containing 10 mg of 1'-[N-(1-S-carbethoxy-3-phenylpropyl)-S-alanyl]-(3'R,5'S)-spirobicyclo[2.2.2]octane-2,3'-pyrrolidine-5'-carboxylic acid are filled with the following mixture:

| | |
|---|---|
| 1'-[N-(1-S-Carbethoxy-3-phenylpropyl)-S-alanyl]-(3'R,5'S)-spirobicyclo[2.2.2]octane-2,3'-pyrrolidine-5'-carboxylic acid | 10 mg |
| Magnesium stearate | 1 mg |
| Lactose | 214 mg |

These capsules can be used for the treatment and prophylaxis of cognitive dysfunctions.

EXAMPLE 4

The preparation of an injection solution is described below:

| | |
|---|---|
| 2-[N-(1-S-Carboxy-3-phenylpropyl)-S-alanyl]-(1S,3S,5S)-2-azabicyclo[3.3.0]octane-2-carboxylic acid | 250 mg |
| Methylparaben | 5 g |
| Propylparaben | 1 g |
| Sodium chloride | 25 g |
| Water for injections | 5 l |

2-[N-(1-S-Carboxy-3-phenylpropyl)-S-alanyl]-(1S,3S,5S)-2-azabicyclo[3.3.0]octane-3-carboxylic acid, the preservatives and sodium chloride are dissolved in 3 l of water for injections, and the solution is made up to 5 l with water for injections. The solution is filtered sterile and dispensed aseptically into presterilized vials, which are closed with sterilized rubber caps. Each vial contains 5 ml of solution.

EXAMPLE 5

Tablets which can be used for the treatment or prophylaxis of cognitive dysfunctions are prepared as described in Example 1 with the exception that in place of 2-[N-(1-S-carbethoxy-3-phenylpropyl)-S-alanyl]-(1S,3S,5S)-2-azabicyclo[3.3.0]octane-3S-carboxylic acid use is made of 2-[N-(1-S-carboxy-3-phenylpropyl)-S-alanyl]-(1S,3S,5S)-2-azabicyclo[3.3.0]octane-3-carboxylic acid or 1-[N-(1-S-carboxy-3-phenylpropyl)-S-alanyl]-(2S,3aR,7aS)-octahydroindole-2-carboxylic acid or 1-[N-(1-S-carbethoxy-3-phenylpropyl)-S-alanyl]-cis-2,3,3a,4,5,7a-hexahydro[1H]indole-2-S-endo-carboxylic acid or 1-[N-(1-S-carboxy-3-phenylpropyl)-S-alanyl]-cis-2,3,3a,4,5,7a-hexahydro[1H]indole-2-S-endo-carboxylic acid or 2-[N-(1-S-carboxy-3-phenylpropyl)-S-lysyl]-(1S,3S,5S)-2-azabicyclo[3.3.0]octane-3-carboxylic acid or 2-[N-(1-S-carbethoxy-3-cyclohexylpropyl)-S-alanyl]-1S,3S,5S)-2-azabicyclo[3.3.0]octane-3-carboxylic acid or N-(1-S-carboxy-3-cyclohexylpropyl)-S-lysyl-(1S,3S,5S)-2-azabicyclo[3.3.0]octane-3-carboxylic acid or 1'-[N-(1-S-carbethoxy-3-phenylpropyl)-S-alanyl]-exo-spirobicyclo[2.2.2]octane-2,3'-pyrrolidin-5'-S-ylcarboxylic acid or (S,S,S)-1-methyl-2-(1-carbethoxy-3-phenylpropyl)-2H-undecahydrocyclopenta[4.5]pyrrolo[1,2-a]pyrazine-3,8-dione or 1'-[N-(1-S-carbethoxy-3-phenylpropyl)-S-alanyl]-endo-spirobicyclo[2.2.2]octane-2,3'-pyrrolidin-5'-S-ylcarboxylic acid.

EXAMPLE 6

An injection solution is prepared in analogy to the procedure described in Example 4 with the exception that in place of 2-[N-(1-S-carbethoxy-3-phenylpropyl)-S-alanyl]-(1S,3S,5S)-2-azabicyclo[3.3.0]octane-3-carboxylic acid use is made of 2-[N-(1-S-carboxy-3-phenylpropyl)-S-alanyl]-(1S,3S,5S)-2-azabicyclo[3.3.0]octane-3-carboxylic acid or 1-[N-(1-S-carbethoxy-3-phenylpropyl)-S-alanyl]-(2S,3aR,7aS)-octahydroindole-2-carboxylic acid hydrochloride or 1-[N-(1-S-carboxy-3-phenylpropyl)-S-alanyl]-(2S,3aR,7aS)-octahydroindole-2-carboxylic acid or 1-[N-(1-S-carbethoxy-3-cyclohexylpropyl)-S-alanyl]-cis-2,3,3a,4,5,7a-hexahydro[1H]indole-2-S-endo-carboxylic acid or 1-[N-(1-S-carboxy-3-phenylpropyl)-S-alanyl]-cis-2,3,3a,4,5,7a-hexahydro[1H]indole-2-S-endo-carboxylic acid or 2-[N-(1-carboxy-3-phenylpropyl)-S-lysyl]-(1S,3S,5S)-2- azabicyclo[3.3.0]octane-3-carboxylic acid or 2-[N-(1-S-carbethoxy-3-cyclohexylpropyl)-S-alanyl]-(1S,3S,5S)-2-azabicyclo[3.3.0]octane-3-carboxylic acid or 2-[N-(1-S-carboxy-3-cyclohexylpropyl)-S-alanyl]-(1S,3S,5S)-2-azabicyclo[3.3.0]octane-3-carboxylic acid or 1'-[N-(1-S-carboxy-3-phenylpropyl)-S-alanyl]-endo-spirobicyclo[2.2.2]octane-2,3'-pyrrolidine-5'-S-carboxylic acid or 1'-[N-(1-S-carboxy-3-phenylpropyl)-S-alanyl]-exo-spirbicyclo[2.2.2]octane-2,3'-pyrrolidine-5'-S-carboxylic acid.

The Examples 7-95 which now follow are intended to illustrate the process according to the invention for the preparation of the new compounds of the formula I and III, without confining the invention to them.

EXAMPLE 7

Octadecyl 2-[N-(1S)-ethoxycarbonyl-3-phenylpropyl-S-alanyl]-cis,endo-2-azabicyclo[3.3.0]octane-3-S-carboxylate 23 g of octadecyl cis,endo-2-azabicyclo[3.3.0]octane-3-carboxylate prepared in analogy to European Patent A-79022 are reacted with 6.7 g of HOBt, 13.8 g of N-(1S)-carbethoxy-3-phenylpropyl-S-alanine and 10.2 g of dicyclohexylcarbodiimide in 200 ml of dimethylformamide. After stirring at room temperature for 3 hours, the precipitated dicyclohexylurea is filtered off with suction, the filtrate is concentrated, the residue is taken up in 1 of ethyl acetate, and the solution is extracted by shaking with 3×500 ml of 5% strength NaHCO₃ solution. The organic phase is concentrated and chromatographed on a column of 1 kg of silica gel with ethyl acetate/petroleum ether in the ratio 2:1, and in this way is separated into the title compound and the diastereomeric (S,S,R) compound.

EXAMPLE 8

1-[N-(1S)-Dodecyloxycarbonyl-3-phenylpropyl-S-alanyl]-2S, 3aR,7aR-octahydroindole-2-carboxylic acid a) Benzyl 1-[N-(1S)-dodecyloxycarbonyl-3-phenylpropyl-S-alanyl]-2S,3aR,7aR-octahydroindole-2-carboxylate 10 mmol of benzyl S-alanyl-2S,3aR,7aR-octahydroindole-2-carboxylate (prepared as in European Patent A-84164) are dissolved in 30 ml of anhydrous ethanol. Ethanolic potassium hydroxide is used to adjust the pH of the solution to 7.0, and 1 g of powdered molecular sieve (4A), and then 10 mmol of dodecyl 2-keto-4-phenylbutyrate, are added. A solution of 1 g of sodium cyanoborohydride in 10 ml of anhydrous ethanol is slowly added dropwise. After a reaction time of 20 hours at 20° to 25° C., the reaction solution is filtered, and the solvent is removed by distillation. The residue is taken up in ethyl acetate/water. After the ethyl acetate phase has been evaporated, the residue is chromatographed on silica gel with ethyl acetate/cyclohexane (1:4).

b)

The compound obtained as in a) is hydrogenated in ethanol in the presence of palladium/animal charcoal (10%) at 20°-25° C. under atmospheric pressure. After the catalyst has been removed, 0.5N ethanolic hydrogen chloride is added to the solution until it gives an acid reaction. The solution is concentrated in vacuo, and the residue is crystallized by trituration with diisopropyl ether.

EXAMPLE 9

Isobutyl 2-[N-[(2S)-ethoxycarbonyl-3-phenylpropyl]-L-alanyl]-(1S,3S,5S)-2-azabicyclo[3.3.0]octane-3-carboxylate 2.00 g (4.80 mmol) of 2-[N-[(1S)-ethoxycarbonyl-3-phenylpropyl]-L-alanyl]-(1S,3S,5S)-2-azabicyclo[3.3.0]octane-3-carboxylic acid were dissolved in 100 ml of isobutanol, 0.1 ml of concentrated sulfuric acid was added, and the mixture was boiled under reflux for 15 hours. After cooling, the solvent was removed in a rotary evaporator, and the residue was taken up in methylene chloride. This solution was washed once with water, once with saturated aqueous NaHCO₃ solution and again with water, dried over MgSO₄, and concentrated, and impurities were removed by chromatography on 200 g of silica gel (mobile phase methylene chloride/ethyl acetate 8:2).

Yield: 51% of theory of oily product.

$[\alpha]_D^{20} = -28.2°$ (c=1, methanol).

This product was dissolved in ether, the pH was adjusted to 2 with saturated ethereal hydrochloric acid, the solvent was evaporated off, and the residue was crystallized from diisopropyl ether.

Data on the hydrochloride:
Melting point 123°-124° C.
$[\alpha]_D^{20} = +17.7°$ (c=1, methanol).

EXAMPLE 10

Benzhydryl 2-[N-[(1S)-ethoxycarbonyl-3-phenylpropyl]-L-alanyl]-(1S,3S,5S)-2-azabicyclo[3.3.0]octane-3-carboxylate 2.07 g (4.97 mmol) of 2-[N-[(1S)-ethoxycarbonyl-3-phenylpropyl]-L-alanyl]-(1S,3S,5S)-2-azabicyclo[3.3.0]octane-3-carboxylic acid were dissolved in 50 ml of acetone and, while cooling in ice, a solution of 1.16 g (5.98 mmol) of diphenyldiazomethane in 50 ml of acetone was added dropwise. The solution was then stirred at room temperature for 26 hours, the solvent was evaporated off in a rotary evaporator, and the residue was purified by flash chromatography on 150 g of silica gel (mobile phase toluene/ethanol 98:2).

Yield: 2.55 g (88%) of oily product,
$[\alpha]_D^{20} = -33.8°$ (c=1, methanol).

EXAMPLE 11

Octadecyl 2-[N-[(1S)-ethoxycarbonyl-3-phenylpropyl]-L-alanyl]-(1S,3S,5S)-2-azabicyclo[3.3.0]octane-3-carboxylate 2.08 g (5.00 mmol) of 2-[N-[(1S)-ethoxycarbonyl-3-phenylpropyl]-L-alanyl]-(1S,3S,5S)-2-azabicyclo[3.3.0]octane-3-carboxylic acid were dissolved in 25 ml of absolute dimethylformamide, 1.00 g (10.0 mmol) of potassium bicarbonate was added, and the mixture was stirred at 40° C. for 90 minutes. After cooling to room temperature, a solution of 4.00 g (12.0 mmol) of 1-bromooctadecane in 20 ml of absolute dimethylformamide was added dropwise, and the mixture was stirred at 40° C. for 4 hours. The solvent was removed in a rotary evaporator at about 1 torr, and the residue was partitioned between water and methylene chloride. The organic phase was separated off, dried over MgSO₄ and concentrated. 3.05 g (92%) of the product were isolated from the crude product (5.40 g) after column chromatography on 200 g of silica gel (mobile phase toluene/ethanol 99:1).

$[\alpha]_D^{20} = -19.6°$ (c=1, methanol).

EXAMPLE 12

Benzyl 2-[N-[(1S)-benzyhydroloxycarbonyl-3-phenylpropyl]-L-alanyl]-(1S,3S,5S)-2-azabicyclo[3.3.0]octane-3-carboxylate a) Benzhydryl (2R)-hydroxy-4-phenylbutyrate A solution of 10.1 g (52.1 mmol) of diphenyldiazomethane in 400 ml of absolute acetone was added dropwise over 20 minutes to a solution of 7.40 g (41.1 mmol) of (2R)-hydroxy-4-phenylbutyric acid in 200 ml of absolute acetone while cooling in ice, and the reaction mixture was stirred at room temperature for 20 hours. The solvent was evaporated off, and the residue was triturated with 100 ml of petroleum ether. 6.4 g of crystalline product were obtained. The mother liquor was concentrated, and a further 6.0 g of the product were isolated by column chromatography on 700 g of silica gel (mobile phase toluene/ethanol 99:1).
Total yield: 12.4 g (87%).
Melting point 88°-89° C.
$[\alpha]_D^{20} = -1.8°$ (c=5, methanol).

b) Benzyl 2-[N-[(1S)-benzhydryloxycarbonyl-3-phenylpropyl]-L-alanyl]-(1S,3S,5S)-2-azabicyclo[3.3.0]octane-3-carboxylate b₁) 1.80 g (4.33 mmol) of benzyl 2-(N-tert.butoxycarbonyl-L-alanyl)-(1S,3S,5S)-2-azabicyclo[3.3.0]octane-3-carboxylate were dissolved in 4.5 ml of trifluoroacetic acid, and the reaction solution was stirred at room temperature for 90 minutes. It was then concentrated and, to remove trifluoroacetic esters, toluene was evaporated off three times in a rotary evaporator. The residue, which comprised 1.90 g of benzyl 2-(L-alanyl)-(1S,3S,5S)-2-azabicyclo[3.3.0]octane-3-carboxylate trifluoroacetate, was dissolved in 10 ml of absolute methylene chloride (solution A).

b₂) 1.63 g (4.71 mmol) of benzhydryl (2R)-hydroxy-4-phenylbutyrate from Example 12 a) were dissolved together with 0.4 ml of absolute pyridine in 25 ml of absolute methylene chloride and, at -10° C., 1.41 g (5.00 mmol) of trifluoromethanesulfonic anhydride were added dropwise within 20 minutes. The cooling bath was then removed and, after room temperature had been reached, the solvent was evaporated off. The residue was filtered through 50 g of silica gel using methylene chloride, and the filtrate was concentrated. 1.70 g of benzhydryl 4-phenyl-(2R)-trifluoromethylsulfonyloxybutyrate were obtained and were dissolved in 10 ml of absolute methylene chloride (solution B).

b₃) 1.0 ml (7.40 mmol) of triethylamine was added to solution A and then, at 0° C., solution B was slowly added dropwise. The cooling bath was removed and the reaction solution was stirred at room temperature for 19 hours, then washed three times with water, dried over MgSO₄ and concentrated. The residue was purified by chromatography on 80 g of silica gel (mobile phase cyclohexane/ethyl acetate 8:2 and 7:3), and 0.95 g (30%) of the desired product was obtained.
Melting point 81°-85° C.
$[\alpha]_D^{20} = -55.2°$ (c=1, methanol).

By suitable combinations of the methods described in the foregoing examples, the following additional compounds are prepared (the designation of the ring systems corresponds to that for the compounds of the general formulae I and II):

| Example | R³OOC—CH—N—<br>　　　　　R⁴　R⁵ | R² | R³ |
|---|---|---|---|
| | R³OOC—CH—N—C—CH—NH—CH—CH₂—CH₂—⌬<br>　　　　　R⁴　R⁵　‖　CH₃　　　COOR²<br>　　　　　　　　O | | |
| 13 | Ring system A | —C₂H₅ | —CH(CH₃)₂ |
| 14 | Ring system B | —C₂H₅ | —CH₂—CH(CH₃)₂ |
| 15 | Ring system C | —CH₃ | —CH₂—⌬  |
| 16 | Ring system C | —C₂H₅ | —CH(C₆H₅)₂ |
| 17 | Ring system D | —C₂H₅ |  |
| 18 | Ring system D | —C₂H₅ | 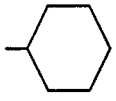 |
| 19 | Ring system D | —C₂H₅ |  |

-continued

| | | | |
|---|---|---|---|
| 20 | Ring system D | —C$_2$H$_5$ | 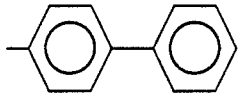 |
| 21 | Ring system D | —C$_2$H$_5$ | 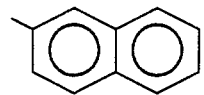 |
| 22 | Ring system D | —C$_2$H$_5$ | —(CH$_2$)$_3$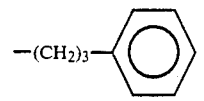 |
| 23 | Ring system E | —C$_2$H$_5$ | —(CH$_2$)$_5$—CH$_3$ |
| 24 | Ring system F | —CH$_3$ | —CH(C$_6$H$_5$)$_2$ |
| 25 | Ring system G | —C$_2$H$_5$ | —CH(CH$_3$)$_2$ |
| 26 | Ring system G | —C$_2$H$_5$ | —CH(C$_6$H$_5$)$_2$ |

$$R^3OOC-\overset{*}{C}H-N-\overset{*}{C}-\overset{*}{C}H-NH-\overset{*}{C}H-CH_2-CH_2-\bigcirc\\ \qquad\qquad\; R^4\;\; R^5\; O\; CH_3\quad\; COOR^2$$

| | | | |
|---|---|---|---|
| 27 | Ring system G | —C$_2$H$_5$ | —(CH$_2$)$_2$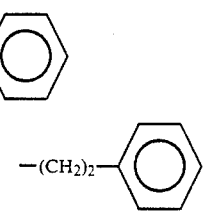 |
| 28 | Ring system H | C$_2$H$_5$ | —CH(CH$_3$)$_2$ |
| 29 | Ring system H | C$_2$H$_5$ | —CH$_2$—CH(CH$_3$)$_2$ |
| 30 | Ring system H | C$_2$H$_5$ | —(CH$_2$)$_5$—CH$_3$ |
| 31 | Ring system H | C$_2$H$_5$ | 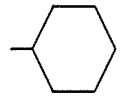 |
| 32 | Ring system H | C$_2$H$_5$ | 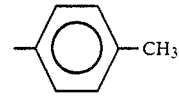 |
| 33 | Ring system H | C$_2$H$_5$ | 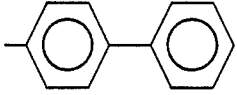 |
| 34 | Ring system H | C$_2$H$_5$ | 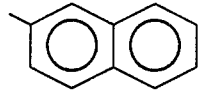 |
| 35 | Ring system H | H | —CH$_2$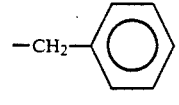 |
| 36 | Ring system H | C$_2$H$_5$ | —CH(C$_6$H$_5$)$_2$ |
| 37 | Ring system H | C$_2$H$_5$ | —(CH$_2$)$_8$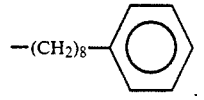 |
| 38 | Ring system I | CH$_3$ | 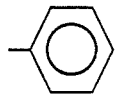 |
| 39 | Ring system J | C$_2$H$_5$ | —CH(C$_6$H$_5$)$_2$ |

-continued

| | | | |
|---|---|---|---|
| 40 | Ring system K | C$_2$H$_5$ | —(CH$_2$)$_4$—CH$_3$ |
| 41 | Ring system L | C$_2$H$_5$ | —C(CH$_3$)$_3$ |
| 42 | Ring system M | C$_2$H$_5$ | —(CH$_2$)$_2$—CH(CH$_3$)$_3$ |
| 43 | Ring system N | C$_2$H$_5$ | —CH(4-F—C$_6$H$_4$)$_2$ |
| 44 | Ring system N | C$_2$H$_5$ | —CH(CH$_3$)$_2$ |
| 45 | Ring system O | C$_2$H$_5$ | 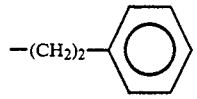 |
| 46 | Ring system P | C$_2$H$_5$ | 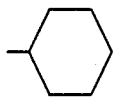 |
| 47 | Ring system Q | C$_2$H$_5$ | 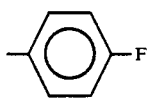 |
| 48 | Ring system A | CH$_2$CH(CH$_3$)$_2$ | 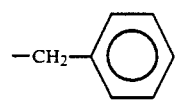 |
| 49 | Ring system B | CH(CH$_3$)$_2$ | —C(CH$_3$)$_3$ |
| 50 | Ring system C | CH(C$_6$H$_5$)$_2$ | —H |
| 51 | Ring system D | CH$_2$— | 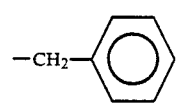 |
| 52 | Ring system D | CH$_2$—CH(CH$_3$)$_2$ | 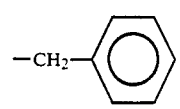 |
| 53 | Ring system D | CH$_2$—CH(CH$_3$)$_2$ | —H |
| 54 | Ring system D | CH$_2$—CH(CH$_3$)$_2$ | —CH(C$_6$H$_5$)$_2$ |
| 55 | Ring system D | CH(C$_6$H$_5$)$_2$ | —C(CH$_3$)$_3$ |
| 56 | Ring system D | CH(C$_6$H$_5$)$_2$ | —H |
| 57 | Ring system E | 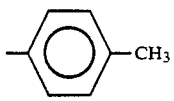 | —(CH$_2$)$_5$—CH$_3$ |
| 58 | Ring system E | —CH$_2$—CH(CH$_3$)$_2$ | —CH(4-F—C$_6$H$_4$)$_2$ |
| 59 | Ring system G | —CH(C$_6$H$_5$)$_2$ | 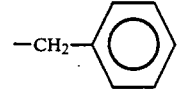 |
| 60 | Ring system G | —CH(C$_6$H$_5$)$_2$ | —C(CH$_3$)$_3$ |
| 61 | Ring system H | —CH$_2$CH(CH$_3$)$_2$ | 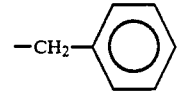 |
| 62 | Ring system H | —CH$_2$CH(CH$_3$)$_2$ | —H |
| 63 | Ring system H | —CH$_2$CH(CH$_3$)$_2$ | —CH(C$_6$H$_5$)$_2$ |
| 64 | Ring system H | 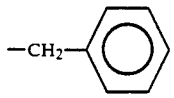 | 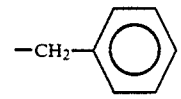 |

| | | | |
|---|---|---|---|
| 65 | Ring system H | 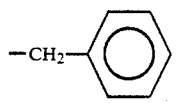 | —C(CH$_3$)$_3$ |
| 66 | Ring system H | —CH(C$_6$H$_5$)$_2$ | 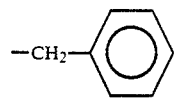 |
| 67 | Ring system H | —CH(C$_6$H$_5$)$_2$ | —H |
| 68 | Ring system H | —CH(C$_6$H$_5$)$_2$ | —C(CH$_3$)$_3$ |
| 69 | Ring system H | —CH(C$_6$H$_5$)$_2$ | —CH(C$_6$H$_5$)$_2$ |
| 70 | Ring system I | 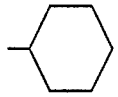 | 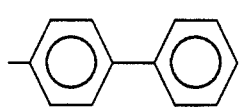 |
| 71 | Ring system J | —(CH$_2$)$_5$—CH$_3$ | —CH(C$_6$H$_5$)$_2$ |
| 72 | Ring system K | 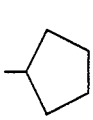 | 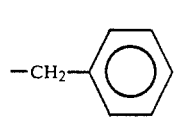 |
| 73 | Ring system L | 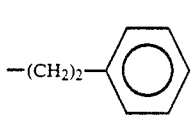 | —(CH$_2$)$_5$—CH$_3$ |
| 74 | Ring system M | —(CH$_2$)$_2$—CH(CH$_3$)$_2$ | —CH(C$_6$H$_5$)$_2$ |
| 75 | Ring system N | —CH(C$_6$H$_5$)$_2$ | —C(CH$_3$)$_2$—CH$_2$CH$_3$ |
| 76 | Ring system O | —CH(CH$_3$)$_2$ | —CH(C$_6$H$_5$)$_2$ |
| 77 | Ring system P | —CH(CH$_3$)$_2$ | —C(CH$_3$)$_3$ |
| 78 | Ring system Q | —C(CH$_3$)$_3$ | 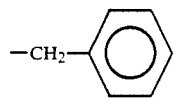 |
| 78a | Ring system D | C$_2$H$_5$ | Menthyl |
| 78b | Ring system G | Menthyl | CH$_2$C$_6$H$_5$ |
| 79 | Ring system O | —CH(C$_6$H$_5$)$_2$ | —CH$_2$SH |
| 80 | Ring system O | —(CH$_2$)$_5$—CH$_3$ | —CH$_2$SH |
| 81 |  | —CH(C$_6$H$_5$)$_2$ | —CH$_2$—S—CO—C(CH$_3$)$_3$ |
| 82 |  | —CH(CH$_3$)$_2$ | —CH$_2$—S—CO—C(CH$_3$)$_3$ |
| 83 | 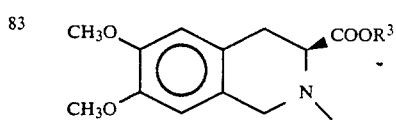 | —CH(C$_6$H$_5$)$_2$ | 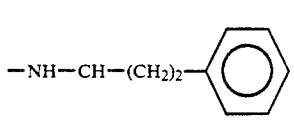 |
| 84 |  | —CH(4-F—C$_6$H$_4$)$_2$ | 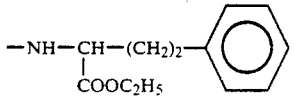 |

-continued

| | | | |
|---|---|---|---|
| 85 | R³OOC—CH₂—N— | 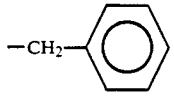 | 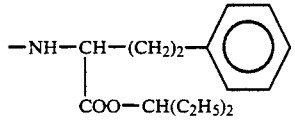 |
| 86 | Ring system H | H | 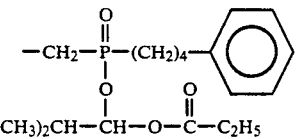 |

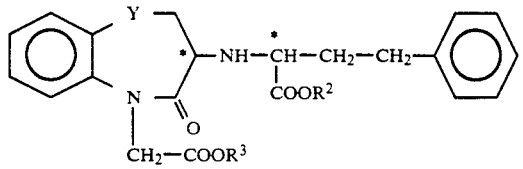

| Example | Y¹ | R² | R³ |
|---|---|---|---|
| 87 | CH₂ | —C₂H₅ | —CH(C₆H₅)₂ |
| 88 | S | —CH(C₆H₅)₂ | —(CH₂)₅—CH₃ |
| 89 | CH₂ | —CH₂—CH(CH₃)₂ | 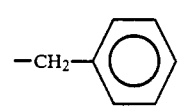 |

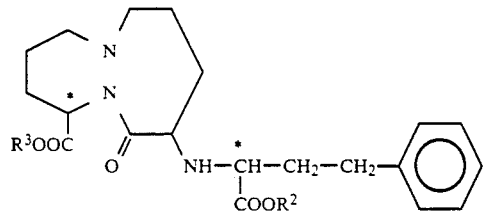

| Example | R² | R³ |
|---|---|---|
| 90 | —CH(C₆H₅)₂ | —C(CH₃)₃ |
| 91 | —CH(C₆H₅)₂ | —CH(C₆H₅)₂ |

EXAMPLE 92

4-[N-(1S)-Carboethoxy-3-phenylpropyl-)-S-benzyl]-exospiro(bicyclo[2.2.2]octane-2,3-pyrrolidine)-5-carboxylic acid a) Benzyl ester of N-(1S-carbethoxy-3-phenylpropyl)-S-leucine 3.4 g (10 mmol) of ethyl 2-(D)-trifluoromethylsulfonyl-oxy-4-phenylbutyrate and 5.9 g (15 mmol) of the benzyl ester of L-leucine tosylate were mixed in 50 ml of abs. CH₂Cl₂ and, after addition of 4.2 ml of triethylamine, the mixture was stirred at room temperature for 6.5 hours. After concentration of the solution, the product was isolated by column chromatography (silica gel, cyclohexane/ethyl acetate 9:1). 3.2 g of colorless oil were obtained.

¹H NMR δ=0.95 (d, CH₃), 1.2 (t, CH₃) 1.8 (m, CH₂) 2.6 (m, CH₂) 3.3 (m, CH) 4.1 (q, CH₂) 5.1 (s, CH₂) 7.3 (s, CH) ppm.

b) N-(1-S-Carboethoxy-3-phenylpropyl)-S-leucine 3.1 g of the benzyl ester obtained in a) were cleaved by hydrogenolysis with 500 mg of Pt/C (10%) in 200 ml of ethanol. After removal of the catalyst by filtration and concentration of the solution, 2.3 g of colorless crystals of the carboxylic acid of melting point 120°–121° C. were obtained.

¹H NMR δ=0.9 (d, CH₃), 1.25 (t, CH₃), 1.8–2.1 (m,CH₂), 2 7 (m, CH₂), 3.3 (q, CH), 4.25 (q, CH₂), 7.2 (.s, CH) ppm.

4-[N-(1S)-Carbethoxy-3-phenylpropyl)-S-leucyl]-exospirobicyclo[2.2.2]octane-2,3-pyrrolidine-5-carboxylic acid 2 g (6.2 mmol) of N-(1-S-carboethoxy-3-phenylpropyl)-S-leucine and 1.9 g (3.9 mmol) of benzyl exo-spiro-(bicyclo[2.2.2]-octane-2,3-pyrrolidine)-5-carboxylate were stirred in 100 ml of dimethylformamide with 4.3 ml of triethylamine and 6.5 ml of n-propylphosphonic anhydride at room temperature overnight. The reaction solution was taken up in ethyl acetate and shaken twice with aqueous NaHCO₃ solution and once each with 10% aqueous citric acid, saturated aqueous NaHCO₃ solution and saturated aqueous NaCl solution. The organic phase was then separated off, dried and concentrated. The crude product, with a yield of 2.8 g, was separated into the two diastereomers by column chromatography (silica gel, toluene/ethyl acetate 95:5). 1 g of pure product was obtained for each benzyl ester. 1 g of the first diastereomer was hydrogenated with Pd/C in 40 ml of ethanol. 780 mg of crystalline carboxylic acid of melting point 131°–132° C. were obtained.

Rotation $[\alpha]_D = -2.8°$ (c=1, methanol).

860 mg of the second diastereomer were hydrogenated with Pd/C in 35 ml of ethanol and, after removal of the catalyst by filtration and concentration of the solution, the yield was 720 mg.

Melting point: the substance sinters above 65° C.

Rotation $[\alpha]_D = -22.2°$ (c=1, methanol).

EXAMPLE 93

4-[N-(1S)-Carboxyl-3-phenylpropyl)-S-leucyl]-exo-spiro-(bicyclo[2.2.2]octane-2,3-pyrrolidine)-5-carboxylic acid 102 mg (0.2 mmol) of the carboxylic acid from Example 92c) were stirred in aqueous 4N KOH solution until all the substance had dissolved. The solution was applied to an ion exchanger ((R)Amberlite R 120) and eluted with a 2% strength solution of pyridine in water. The yield was 70 mg.

Rotation $[\alpha]_D^{20} = +3.9°$ (c=1, methanol).

The following compounds of the formula II are prepared in analogous manner (the designations of the ring systems correspond to those for the compounds of the general formulae I and II):

HOOC—CH—N—C—CH—CH—CH$_2$—CH$_2$—C$_6$H$_5$
       |    |  ||  |    |
       R$^4$ R$^5$ O R$^1$ COOC$_2$H$_5$

| R$^1$ | HOOC—CH—NH (R$^4$, R$^5$) |
|---|---|
| CH(CH$_3$)$_2$ | A |
| CH(CH$_3$)CH$_2$CH$_3$ | A |
| CH$_2$C$_6$H$_5$ | A |
| CH$_2$—C$_6$H$_{11}$ (CH$_2$-Cyclohexyl) | C |
| CH$_2$—C$_6$H$_4$—OCH$_3$ | G |
| CH$_2$—C$_6$H$_4$—OC$_2$H$_5$ | C |
| CH$_2$—C$_6$H$_4$—OC$_3$H$_7$ | C |
| CH$_2$—C$_6$H$_4$—OC$_4$H$_9$ | A |
| (CH$_2$)$_4$—NH$_2$ | D |
| (CH$_2$)$_3$—NH$_2$ | A |
| CH$_2$—CH$_2$—S—CH$_3$ | A |
| CH$_2$—C(=CH—CH=)S (thiophene ring) | A |
| CH(CH$_3$)$_2$ | B |
| CH(CH$_3$)CH$_2$CH$_3$ | B |
| CH$_2$C$_6$H$_5$ | B |
| CH$_2$—C$_6$H$_{11}$ | D |
| CH$_2$—C$_6$H$_4$—OCH$_3$ | H |
| CH$_2$—C$_6$H$_4$—OC$_2$H$_5$ | G |
| CH$_2$—C$_6$H$_4$—On-C$_3$H$_7$ | G |
| CH$_2$—C$_6$H$_4$—On-C$_4$H$_9$ | C |
| (CH$_2$)$_4$—NH$_2$ | C |
| (CH$_2$)$_3$—NH$_2$ | G |
| CH$_2$—CH$_2$—S—CH$_3$ | D |
| CH$_2$—C(=CH—CH=)S | B |
| CH(CH$_3$)$_2$ | C |
| CH(CH$_3$)CH$_2$CH$_3$ | C |
| CH$_2$C$_6$H$_5$ | C |
| CH$_2$—C$_6$H$_{11}$ | E |
| CH$_2$—C$_6$H$_4$—OCH$_3$ | I |
| CH$_2$—C$_6$H$_4$—OC$_2$H$_5$ | H |
| CH$_2$—C$_6$H$_4$—On-C$_3$H$_7$ | H |

-continued

HOOC—CH—N—C—CH—CH—CH$_2$—CH$_2$—C$_6$H$_5$
       |    |  ||  |    |
       R$^4$ R$^5$ O R$^1$ COOC$_2$H$_5$

| R$^1$ | HOOC—CH—NH (R$^4$, R$^5$) |
|---|---|
| CH$_2$—C$_6$H$_4$—On-C$_4$H$_9$ | G |
| (CH$_2$)$_4$—NH$_2$ | G |
| (CH$_2$)$_3$—NH$_2$ | H |
| CH$_2$—CH$_2$—S—CH$_3$ | H |
| CH$_2$—C(=CH—CH=)S | C |
| CH(CH$_3$)$_2$ | D |
| CH(CH$_3$)CH$_2$CH$_3$ | D |
| CH$_2$C$_6$H$_5$ | D |
| CH$_2$—C$_6$H$_{11}$ | F |
| CH$_2$—C$_6$H$_4$—OCH$_3$ | N |
| CH$_2$—C$_6$H$_4$—OC$_2$H$_5$ | I |
| CH$_2$—C$_6$H$_4$—On-C$_3$H$_7$ | I |
| CH$_2$—C$_6$H$_4$—On-C$_4$H$_9$ | H |
| (CH$_2$)$_4$—NH$_2$ | H |
| (CH$_2$)$_3$—NH$_2$ | O |
| CH$_2$—CH$_2$—S—CH$_3$ | I |
| CH$_2$—C(=CH—CH=)S | D |
| CH(CH$_3$)$_2$ | G |
| CH(CH$_3$)CH$_2$CH$_3$ | E |
| CH$_2$C$_6$H$_5$ | H |
| CH$_2$—C$_6$H$_{11}$ | G |
| CH$_2$—C$_6$H$_4$—OCH$_3$ | O |
| CH$_2$—C$_6$H$_4$—OC$_2$H$_5$ | N |
| CH$_2$—C$_6$H$_4$—On-C$_3$H$_7$ | N |
| CH$_2$—C$_6$H$_4$—On-C$_4$H$_9$ | I |
| (CH$_2$)$_4$—NH$_2$ | N |
| (CH$_2$)$_3$—NH$_2$ | P |
| CH$_2$—CH$_2$—S—CH$_3$ | P |
| CH$_2$—C(=CH—CH=)S | K |
| CH(CH$_3$)$_2$ | H |
| CH(CH$_3$)CH$_2$CH$_3$ | F |
| CH$_2$C$_6$H$_5$ | I |
| CH$_2$—C$_6$H$_{11}$ | H |
| CH$_2$—C$_6$H$_4$—OCH$_3$ | P |
| CH$_2$—C$_6$H$_4$—OC$_2$H$_5$ | O |
| CH$_2$—C$_6$H$_4$—On-C$_3$H$_7$ | O |
| CH$_2$—C$_6$H$_4$—On-C$_4$H$_9$ | N |
| (CH$_2$)$_4$—NH$_2$ | Q |
| (CH$_2$)$_3$—NH$_2$ | Q |
| CH$_2$—CH$_2$—S—CH$_3$ | Q |
| CH$_2$—C(=CH—CH=)S | G |
| CH(CH$_3$)$_2$ | I |
| CH(CH$_3$)CH$_2$CH$_3$ | G |
| CH$_2$C$_6$H$_5$ | N |
| CH$_2$—C$_6$H$_{11}$ | I |
| CH$_2$—C$_6$H$_4$—OCH$_3$ | Q |
| CH$_2$—C$_6$H$_4$—OC$_2$H$_5$ | P |
| CH$_2$—C$_6$H$_4$—On-C$_3$H$_7$ | P |
| CH$_2$—C$_6$H$_4$—On-C$_4$H$_9$ | O |
| (CH$_2$)$_4$—NH$_2$ | P |
| CH$_2$—CH$_2$—S—CH$_3$ | N |

-continued

HOOC—CH(R4)—N(R5)—C(=O)—CH(R1)—CH(COOC2H5)—CH2—CH2—C6H5

| R1 | HOOC—CH(R4)—NH(R5) |  |
|---|---|---|
| CH₂—C(S)=CH—CH= (ring) |  | H |
| CH(CH₃)₂ |  | O |
| CH(CH₃)CH₂CH₃ |  | H |
| CH₂C₆H₅ |  | O |
| CH₂—C₆H₁₁ |  | L |
| CH₂—C₆H₄—OC₂H₅ |  | Q |
| CH₂—C₆H₄—On-C₃H₇ |  | Q |
| CH₂—C₆H₄—On-C₄H₉ |  | P |
| CH₂—CH₂—S—CH₃ |  | G |
| CH₂—C(S)=CH—CH= (ring) |  | I |
| CH(CH₃)₂ |  | P |
| CH₂—C₆H₅ |  | P |
| CH₂—C₆H₁₁ |  | M |
| CH₂—C₆H₄—OCH₃ |  | D |
| CH₂—C₆H₄—OC₂H₅ |  | D |
| CH₂—C₆H₄—On-C₃H₇ |  | D |
| CH₂—C₆H₄—On-C₄H₉ |  | Q |
| CH₂—C(S)=CH—CH= (ring) |  | N |
| CH(CH₃)₂ |  | N |
| CH(CH₃)CH₂CH₃ |  | P |
| CH₂—C₆H₅ |  | Q |
| CH₂—C₆H₁₁ |  | N |
| CH₂—C₆H₄—On-C₄H₉ |  | D |
| CH₂—C(S)=CH—CH= (ring) |  | P |
| CH(CH₃)CH₂CH₃ |  | Q |
| CH(CH₃)CH₃CH₃ |  | I |
| CH₂—C₆H₁₁ |  | O |
| CH₂—C₆H₁₁ |  | Q |

EXAMPLE 94

1-[N-(1S)-Carboethoxybutyl)-S-alanyl]-octahydrocyclopenta[b]pyrrole)-2-carboxylic acid a) Ethyl DL-2-trifluoromethylsulfonyloxypentanoate 5 g (34 mmol) of ethyl 2-hydroxyvalerate and 2.85 g (35.9 mmol) of absolute pyridine were dissolved in 100 ml of absolute CH₂Cl₂ under protective gas, the solution was cooled to 0° C. and 9.66 g (34 mmol) of trifluoromethanesulfonic anhydride were added. The mixture was warmed to room temperature and stirred for 6 hours. The solution was concentrated and the resulting crude product was purified by column chromatography (silica gel, petroleum ether/CH₂Cl₂ 6:1). The yield was 9.3 g of a colorless, slightly viscous liquid.

IR: 2880–3000, 1770, 1420, 1200–1220, 1150, 620 cm⁻¹.

b) Benzyl ester of N-(1-S-carboethoxybutyl)-S-alanine 4.9 g (17.6 mmol) of the trifluoromethanesulfonic ester thus obtained were dissolved, under nitrogen, in 70 ml of absolute CH₂Cl₂ with 4.08 g of the benzyl ester of L-alanine hydrochloride (19 mmol) with the addition of 5.4 ml of triethylamine, and the solution was stirred at room temperature for 3 hours. It was then concentrated, the crude product was taken up in ethyl acetate, and the solution was washed three times with water, dried and concentrated. The diastereomers were separated by column chromatography (silica gel, cyclohexane/ethyl acetate 5:1). The yield of each isomer was 500 mg. The diastereomer isolated in the first filtration had the S,S configuration.

¹H NMR δ=0.9 (t,CH₃), 1.3 (t,CH₃), 1.35 (d,CH₃), 1.4 (m,CH₂), 1.6 (m,CH₂), 1.9 (s,NH), 3.3 (t,CH), 3.4 (q,CH), 4.2 (m,CH₂), 5.15 (q,CH₂ Ph), 7.4 (s, CH aromat.) ppm.

c) N-(1-S-Carboethoxybutyl)-S-alanine 600 mg (1.95 mmol) of benzyl ester (diastereomer A) were hydrogenated with Pd on charcoal in 34 ml of ethanol. The catalyst was then filtered off, and the solution was concentrated in vacuo. The product was then obtained as a white solid with a melting point of 137° and a yield of 430 mg.

d) 430 mg (1.98 mmol) of N-(1-S-carboethoxybutyl)-S-alanine and 486 mg (1.98 mmol) of benzyl L(−)-octahydrocyclopenta[b]pyrrole-2-carboxylate were dissolved, under nitrogen, in 20 ml of dimethylformamide, the solution was cooled to −10° C., and 1.5 ml of triethylamine and 2 ml of n-propylphosphonic anhydride were added. The solution was stirred at −10° C. for 1 hour and then at room temperature overnight. It was then taken up in 200 ml of ethyl acetate and washed with saturated aqueous NaHCO₃ solution, 10% aqueous citric acid and saturated aqueous NaCl solution. After the solution had been dried and concentrated, the diastereomeric compounds were separated by column chromatography (silica gel, cyclohexane/ethyl acetate 9:1). The yield was 360 mg. Both diastereomers were hydrogenated with Pd/C in ethanol as described in Example 94 c) and, after concentration of the solution, they were obtained as white solids.

EXAMPLE 95

1-[N-(1S)-Carboxybutyl)-S-alanyl]-(octahydrocyclopenta[b]pyrrole)-2-carboxylic acid 60 mg (0.17 mmol) of carboxylic acid (Example 94 d) were stirred into 2 ml of 4N aqueous KOH solution until the substance had completely dissolved. The solution was then applied to a strongly acid ion exchanger and eluted with a 2% strength solution of pyridine in water. The yield after concentration of the solution was 39 mg.

In analogy to the compounds prepared in Examples 94 and 95, it is possible to synthesize the following additional compounds of the formula II

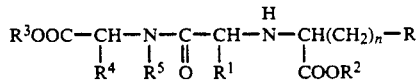

in which, with n=2, R¹ is CH₃, R² C₂H₅, R³ is H, and R and the part of the molecule

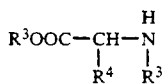

are substituted as indicated in the table detailed below.

| R | HOOC—CH—NH, R⁴, R⁵ |
|---|---|
| CH₃ | A |
| —CH₂CH₂CH₃ | A |
| —(CH₂)₉—CH₃ | C |
| 2-Naphthyl | D |
| 4-Biphenylyl | A |
| —(CH₂)₁₃—CH₃ | A |
| CH₃ | B |
| —CH₂CH₂CH₃ | B |
| —(CH₂)₉—CH₃ | D |
| 2-Naphthyl | F |
| 4-Biphenylyl | C |
| —(CH₂)₁₃—CH₃ | B |
| CH₃ | C |
| —CH₂CH₂CH₃ | C |
| —(CH₂)₉—CH₃ | G |
| 2-Naphthyl | G |
| 4-Biphenylyl | D |
| —(CH₂)₁₃—CH₃ | C |
| CH₃ | D |
| —CH₂CH₂CH₃ | D |
| —(CH₂)₉—CH₃ | H |
| 2-Naphthyl | H |
| 4-Biphenylyl | H |
| —(CH₂)₁₃—CH₃ | D |
| CH₃ | G |
| —CH₂CH₂CH₃ | G |
| —(CH₂)₉—CH₃ | K |
| 2-Naphthyl | I |
| 4-Biphenylyl | L |
| —(CH₂)₁₃—CH₃ | G |
| CH₃ | H |
| —CH₂CH₂CH₃ | H |
| —(CH₂)₉—CH₃ | N |
| 2-Naphthyl | M |
| 4-Biphenylyl | N |
| —(CH₂)₁₃—CH₃ | N |
| CH₃ | N |
| —CH₂CH₂CH₃ | N |
| —(CH₂)₉—CH₃ | O |
| 2-Naphthyl | N |
| 4-Biphenylyl | P |
| —(CH₂)₁₃—CH₃ | O |
| CH₃ | Q |
| —CH₂CH₂CH₃ | Q |
| —(CH₂)₉—CH₃ | P |

-continued

| R | HOOC—CH—NH, R⁴, R⁵ |
|---|---|
| 4-Biphenylyl | Q |
| —(CH₂)₁₃—CH₃ | P |
| CH₃ | P |
| —CH₂CH₂CH₃ | P |
| —(CH₂)₉—CH₃ | Q |
| 4-Biphenylyl | G |
| —(CH₂)₁₃—CH₃ | Q |
| 4-Biphenylyl | H |

We claim:

1. A process for the treatment of a cognitive dysfunction in a mammal, comprising the step of administering to a mammal for the purpose of said treatment, an effective amount of an angiotension-converting enzyme inhibitor of the formula (II) or a physiologically tolerated salt thereof,

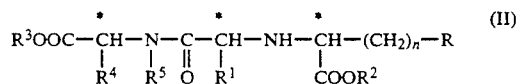

in which n is 1 or 2;

R denotes hydrogen, an aliphatic radical having 1–21 carbon atoms, an aromatic radical having 6–12 carbon atoms, R¹ denotes hydrogen, an aliphatic radical having 1–21 carbon atoms, or, if not already covered by the above definitions, the side-chain, protected where necessary, of a naturally occurring α-amino acid, R² and R³ are identical or different and denote hydrogen, an aliphatic radical having 1–21 carbon atoms, an alicyclic radical having 3—20 carbon atoms, an aromatic radical having 6.14 12 carbon atoms, an araliphatic radical having 7–32 carbon atoms, and R⁴ and R⁵ form, together with the atoms carrying them, a heterocyclic ring system selected from pyrrolidine, octahydroindole, and octahydrocyclopenta[b]pyrrole.

2. The process as claimed in claim 1, wherein said compound of formula (II) is (S,S,S,S,S)-1-[N-(1-carbethoxy-3-phenylpropyl)-alanyl]-octahydroindole-2-carboxylic acid, 1-[N-(1-S-carbethoxy-3-phenylpropyl)-S-alanyl]-(2S,3aR,7aS)-octahydroindole-2-carboxylic acid, or (S,S,S,S,S)-2-[N-(1-carbethoxy-3-phenylpropyl)-alanyl]-2-azabicyclo[3.3.0]-octane-3-carboxylic acid.

* * * * *

UNITED STATES PATENT AND TRADEMARK OFFICE
CERTIFICATE OF CORRECTION

PATENT NO. : 5,231,084
DATED : July 27, 1993
INVENTOR(S) : Franz Hock et al.

It is certified that error appears in the above-indentified patent and that said Letters Patent is hereby corrected as shown below:

Abstract, line 1, change "comoounds" to --compunds--.

Claim 1, column 48, line 39, change "6.14 12" to --6-12--.

Signed and Sealed this

Fourth Day of October, 1994

Attest:

BRUCE LEHMAN

Attesting Officer

Commissioner of Patents and Trademarks